United States Patent [19]
Neurath et al.

[11] Patent Number: 6,165,493
[45] Date of Patent: *Dec. 26, 2000

[54] "METHODS AND COMPOSITIONS FOR DECREASING THE FREQUENCY OF HIV, HERPESVIRUS AND SEXUALLY TRANSMITTED BACTERIAL INFECTIONS"

[75] Inventors: Alexander Robert Neurath, New York; Shibo Jiang, Jackson Heights; Asim Kumar Debnath, New York; Nathan Strick, Oceanside, all of N.Y.; Gordon Jay Dow, Santa Rosa, Calif.

[73] Assignee: New York Blood Center, Inc., New York, N.Y.

[ * ] Notice: This patent is subject to a terminal disclaimer.

[21] Appl. No.: 09/175,909
[22] Filed: Oct. 20, 1998

Related U.S. Application Data

[63] Continuation-in-part of application No. 09/112,130, Jul. 8, 1998, Pat. No. 5,985,313.
[60] Provisional application No. 60/062,936, Oct. 22, 1997, and provisional application No. 60/071,017, Jan. 13, 1998.
[51] Int. Cl.[7] .............................. A61F 13/02; A61F 6/06; A61F 6/14; A61K 9/70; A61K 9/16
[52] U.S. Cl. .......................... 424/434; 424/430; 424/431; 424/432; 424/433; 424/435; 424/436; 424/443; 424/494
[58] Field of Search .................................. 424/430, 431, 424/432, 433, 435, 436, 494

[56] References Cited

U.S. PATENT DOCUMENTS

| | | |
|---|---|---|
| 4,330,338 | 5/1982 | Banker . |
| 4,385,078 | 5/1983 | Onda et al. . |
| 4,462,839 | 7/1984 | McGinley et al. . |
| 4,518,433 | 5/1985 | McGinley et al. . |
| 4,960,814 | 10/1990 | Wu et al. . |
| 4,968,350 | 11/1990 | Bindschaedler et al. . |

(List continued on next page.)

OTHER PUBLICATIONS

Neurath, et al., "3–Hydroxyphthaloyl–β–lactoglobulin. I. Optimization of production and comparison with other compounds considered for chemoprophylaxis of mucosally transmitted human immunodeficiency virus type 1", *Antiviral Chemistry & Chemotherapy*, 1196, vol. 8(2), pp. 131–139.

Neurath, et al., "3–Hydroxyphthaloyl–β–lactoglobulin. II. Anti–human immunodeficiency virus type 1 activity in in vitro environments relevant to prevention of sexual transmission of the virus", *Antiviral Chemistry & Chemotherapy*, 1997, vol. 8(2); pp. 141–148.

Neurath, et al., "A herpesvirus inhibitor from bovine whey", *The Lancet*, vol. 347, Jun. 15, 1996, p. 1703.

Jiang, et al., "Virucidal and Antibacterial Activities of 3–HP–β–LG", 1997, *Vaccines 97*, p. 327–330.

Jiang, et al, Chemically Modified Bovine β–Lactoglobulin Blocks Uptake of HIV–1 by Colon–and Cervix–Derived Epithelial Cell Lines, *Journal of Acquired Immune Deficiency Syndromes and Human Retrovirology*, 1996, vol. 13, pp. 461–462.

(List continued on next page.)

*Primary Examiner*—Carlos A. Azpuru
*Attorney, Agent, or Firm*—Frishauf, Holtz, Goodman, Langer & Chick, P.C.

[57] ABSTRACT

A method for decreasing the frequency of transmission of human immunodeficiency virus or herpesviruses or for preventing the transmission of or treating a sexually transmitted bacterial infection by administering to a human an anti-human immunodeficiency virus amount or an anti-herpesvirus amount or an anti-bacterial amount of cellulose acetate phthalate (CAP) or hydroxypropyl methylcellulose phthalate (HPMCP), such as in micronized form, or a combination thereof, either alone or in combination with a pharmaceutically acceptable carrier or diluent. The CAP and/or HPMCP may be employed as a suspension of micronized particles and may further contain a water miscible, non-solvent for CAP or HPMCP, such as glycerol.

45 Claims, 8 Drawing Sheets

U.S. PATENT DOCUMENTS

| | | |
|---|---|---|
| 5,025,004 | 6/1991 | Wu et al. . |
| 5,326,572 | 7/1994 | Mehra et al. . |
| 5,356,634 | 10/1994 | Wu et al. . |
| 5,380,790 | 1/1995 | Chen et al. . |
| 5,512,092 | 4/1996 | Maruyama et al. . |
| 5,646,151 | 7/1997 | Kruse et al. . |
| 5,723,151 | 3/1998 | Cook et al. . |

OTHER PUBLICATIONS

Neurath, et al., "Bovine β–lactoglobulin modified by 3–hydroxyphthalic anhydride blocks the CD 4 cell receptor for HIV", *Nature Medicine*, vol. 2, No. 2, Feb. 1996, pp. 230–234.

A.R. Neurath, N. Strick, K. Lin, Y. –Y. Li, A.K. Debnath and S. Jiang, "Microbicide B195", 12th World AIDS Conference, Geneva (Switzerland), Jun. 28–Jul. 3, 1998, 239–242.

"METHODS AND COMPOSITIONS FOR DECREASING THE FREQUENCY OF HIV, HERPESVIRUS AND SEXUALLY TRANSMITTED BACTERIAL INFECTIONS"

CROSS-REFERENCE TO RELATED APPLICATIONS

The present application is a continuation-in-part application of application Ser. No. 09/112,130 filed Jul. 8, 1998, now U.S. Pat. No. 5,985,313 wherein priority under 35 USC 119 (e) is claimed for provisional application Nos. 60/062,936 filed Oct. 22, 1997 and 60/071,017, filed Jan. 13, 1998.

BACKGROUND OF THE INVENTION

1. Field of the Invention

The present invention concerns methods for decreasing the frequency of transmission of viral infection, such as human immunodeficiency virus and herpesvirus, and for preventing and treating sexually transmitted bacterial infections, such as *Chlamydia trachomatis*, by administration of cellulose acetate phthalate or hydroxypropyl methylcellulose phthalate, which were heretofore employed as pharmaceutical excipients.

2. Background Information a. Pharmaceutical Excipients

Pharmaceutical excipients are defined as inert substances that form a vehicle for drug delivery (*Webster's Ninth New Collegiate Dictionary,* Merriam-Webster Inc. Publishers, Springfield, Mass., USA, 1985, p. 432). Thus, excipients convert pharmacologically active compounds into pharmaceutical dosage forms suitable for administration to patients. Some excipients are also used for the formulation or production of confectionery, cosmetics and food products. Therefore, approved excipients are used frequently and at higher dosage levels in comparison with most drugs. Excipients are also much less expensive and more easily produced in very large scale in comparison with most drugs.

b. Sexually Transmitted Diseases ("STDs"): An Overview

The human immunodeficiency virus (HIV) pandemic is sustained and progressing predominantly due to sexual transmission of the virus (Mann, J.. M., Tarantola, D. J. M., Netter, T. W., "AIDS in the World", Cambridge: Harvard University Press, (1992)), facilitated by prior infection with other STD pathogens (Perine, P. L., "Sexually Transmitted Diseases in the Tropics", *Med. J. Aust.,* 160, (1994), 358–366).

The urgent need to prevent the transmission of STDs has become highlighted by the HIV/AIDS epidemic, resulting so far in infection of approximately 42 million people and in approximately 12 million deaths (UNAIDS and WHO, Report on the global HIV/AIDS epidemic, Geneva: Joint United Nations Programme on HIV/AIDS, Jun. 1, 1998). The facts that HIV infections are not curable as of now, have become the leading cause of death among young adults and has decreased life expectancy in a number of countries, and the observation that several non-viral STDs facilitate HIV infection, have further emphasized the pressing need for new preventive approaches.

Treatment of STDs (other than HIV) was found to be a feasible and economically justifiable approach to decreasing the rate of HIV-1 transmission (St. Louis, M. E., Levine, W. C., Wasserheit, J. N. et al, "HIV Prevention Through Early Detection and Treatment of Other Sexually Transmitted Diseases—United States Recommendation of the Advisory Committee for HIV and STD Prevention", *Mor. Mort. Wkly. Rep.,* (1998), 47 (No. RR-12), 1–24; Over, M., Piot, P., "Human Immunodeficiency Virus Infection and Other Sexually Transmitted Diseases in Developing Countries: Public Health Importance and Priorities for Resource Allocation", *J. Infect. Dis.,* (1996), 174 (Suppl. 2), 162–175). However, this beneficial approach is not sufficient to control the spread of STDs, including HIV-1.

In the absence of prophylactic vaccines against STD pathogens and HIV in the foreseeable future, and of safe anti-HIV-1 drugs affordable in developing countries, other simple methods to control the sexual transmission of STDs, including HIV-1, must be applied. This includes mechanical (condom) and chemical barrier methods and combinations thereof. Formulations of spermicides shown in vitro to inactivate STD pathogens have been considered for this purpose, but based on the outcome of clinical safety and efficacy trials, their utility remains in doubt.

The use of chemical barrier methods (topical "microbicides") under the control of women has been proposed as a method to control the sexual transmission of HIV-1 and other STDs (Alexander, N. J., "Barriers to Sexually Transmitted Diseases", *Scientific American & Medicine,* (1996), 3:32–41). The fastest way to introduce topical microbicides into practice appeared to be the application of over-the-counter (OTC) contraceptives containing the detergent nonoxynol-9 (N-9). N-9 was shown to inactivate in vitro HIV-1 (Hicks, D. R., Martin, L. S., Getchell, J. P. et al., "Inactivation of HTLV-III/LAV-infected Cultures of Normal Human Lymphocytes by Nonoxynol-9 in vitro", *Lancet,* (1985), 2:1422–1423; Jennings, R., Clegg, A., "The Inhibitory Effect of Spermicidal Agents on Replication of HSV-2 and HIV-1 in vitro", *J. Antimicrob. Chemother.,* (1993), 32:71–82), HSV-2 (Sugarman, B., Mummaw, N., "Effects of Antimicrobial Agents on Growth and Chemotaxis of *Trichomonas Vaginalis"*, *Antimicrob. Agents Chemother.,* (1988), 32:1323–1326) and *Chlamydia trachomatis* (Lyons, J. M., Ito, J. I., Jr., "Reducing the Risk of *Chlamydia Trachomatis* Genital Tract Infection by Evaluating The Prophylactic Potential of Vaginally Applied Chemicals", *Clin. Infect. Dis.,* (1995), 21 (Suppl. 2): S174–S177). N-9 was also found to be cytotoxic. This approach seems to be hampered by clinical data suggesting the adverse effects of some N-9 formulations (Stafford, M. K., Ward, H., Flanagan, A., et al., "Safety Study of Nonoxynol-9 As A Vaginal Microbicide: Evidence of Adverse Effects", *J. Acquir. Imm. Defic. Synd. Hum. Retrovir.,* (1998), 17:327–331; Rosenstein, I. J., Stafford, M. K., Kitchen, V. S. et al., "Effects on Normal Vaginal Flora of Three Intravaginal Microbicidal Agents Potentially Active Against Human Immunodeficiency Virus Type 1", *J. Infect. Dis.,* (1998), 177:1386–1390; Kilmarx, P. H., Limpakarnjanarat, K., Supawitkul, S. et al., "Mucosal Disruption Due To Use of A Widely-distributed Commercial Vaginal Product: Potential to Facilitate HIV Transmission", *AIDS,* (1998), 12:767–773) and lack of efficacy in decreasing the rate of heterosexual HIV-1, gonorrhea and *chlamydia* transmission by one of the N-9 formulations (Roddy, R. E., Zekeng, L., Ryan, K. A. et al., "A Controlled Trial of Nonoxynol 9 Film to Reduce Male-to-Female Transmission of Sexually Transmitted Diseases", *N. Engl. J. Med.,* (1998), 339, 504–510). This indicates that other microbicidal compounds have to be tested as prophylactic agents against HIV-1 and other STDs.

Considering the urgency in controlling the HIV epidemic, the rapid development of other microbiocidal formulations is needed. The introduction of such microbicide formulations into practice would be significantly enhanced by using active ingredients with an already establshed safety record for human use.

To search for safe microbicide formulations, criteria distinct from those applied to screening for anti-HIV-1 drugs have to be used, raising the possibility that promising microbicides with anti-HIV-1 activity may heretofore have been missed during extensive screening for therapeutic anti-HIV-1 compounds. The criteria for selection of anti-HIV-1 microbicides, as compared with those for therapeutic anti-HIV drugs, can be summarized as follows: (a) undesirability of systemic spread leading to preferred consideration of high molecular weight compounds ($M_w \geq 2$ kD), which are active selectively at the site of application; (b) high degree of safety and lack of side effects (due to repeated use by healthy people -as compared with the use of therapeutic anti-HIV-1 drugs by already infected individuals), the safety being augmented by the lack of systemic spread; (c) consideration of compounds with lower specific antiviral activity, which can be compensated for by higher concentrations of the compounds with established safety, and (d) activity directed to early steps in injection and, preferably, direct pathogen inactivation, as implied by the term "microbicide".

Compounds meeting at least some of these criteria are as follows: (a) sulfated polysaccharides (Javan, C. M., Gooderham, N. J., Edwards, R. J. et al., "Anti-HIV Type 1 Activity of Sulfated Derivatives of Dextrin Against Primary Viral Isolates of HIV Type 1 in Lymphocytes and Monocyte-Derived Macrophages", *AIDS Res. Human Retroviruses*, (1997), 13, 875–880; Stafford, M. K., Cain, D., Rosenstein, I., et al., "A Placebo-Controlled, Double Blind Prospective Study in Healthy Female Volunteers of Dextrin Sulphate Gel: A Novel Potential Intravaginal Virucide", *J. Acquir. Immune Defic. Syndr. Hum. Retrovirol.*, (1997), 14, 213–218; Zacharopoulos, V. R., Phillips, D. M., "Vaginal Formulations of Carrageenan Protect Mice From Herpes Simplex Virus Infection", Clin. Diagn. Lab. Immunol., (1997), 4, 465–468; Carlucci, M. J., Pujol, C. A., Ciancia, M. et al., "Antiherpetic and Anticoagulant Properties of Carrageenans From the Red Seaweed Gigartina Skottsbergii and Their Cyclized Derivatives: Correlation Between Structure and Biological Activity", *Int. J. Biol. Macromol., (1997), 20, 97–105*) and other sulfonated polymers (however, the virucidal and bacterial activity of these compounds has not been established and their activity is ascribed to their ability to interact with target cells to inhibit virus entry (Rusconi, S., Moonis, M., Merill, D. P. et al., "Naphthalene Sulfonate Polymers With CD-4-Blocking and Anti-Human Immunodeficiency Virus Type 1 Activities", *Anticrob. Agents Chemother., (1996), 40, 234–236*; McClure, M. O., Moore, J. P., Blanc, D. F. et al., "Investigations into the Mechanism By Which Sulfated Polysaccharides Inhibit HIV Infection In Vitro", *AIDS Res. Hum. Retroviruses, (1992), 8, 19–26*); and (b) protegrins which have broad spectrum activity against bacteria and enveloped viruses (Tamamura, H., Murakami, T., Horiuchi, S. et al., "Synthesis of Protegrin-Related Peptides and Their Antibacterial and Anti-Human Immunodeficiency Virus Activity", *Chem. Pharm. Bull.*, (Tokyo), (1995), 43, 853–858; Lehrer, R. I., Ganz, T., "Endogenous Vertebrate Antibiotics, Defensins, Protegrins, and Other Cysteine-Rich Antimicrobial Peptides", *Ann. N.Y., Acad. Sci.*, (1996), 797, 228–239; Qu, X. D., Harwig, S. S., Shafer, W. M. et al., "Protegrin Structure and Activity Against Neisseria Gonorrhoeae", *Infect. Immun.*, (1997), 65, 636–639), but they also have undesirable activity against Lactobacilli and their application may have economical disadvantages, as compared with that of sulfated polymers.

Since efficacious topical "microbicides" would be expected to be used repeatedly over decades, they should have an established safety record and should preferably not be spread systemically after topical application. They should have the following characteristics: (a) be inexpensive, (b) be produced from widely available resources, (c) have a broad specificity resulting in prevention of transmission of several STDs, and (d) inactivate the infectivity of the respective STD pathogens. In accordance with these requirements, some of the present inventors recently developed a potent anti-HIV and anti-herpesvirus agent, suitable for incorporation into topical gels/creams (Neurath, A. R., Jiang, S., Strick, N. et al., "Bovine β-Lactoglobulin Modified by 3-Hydroxyphthalic Anhydride Blocks the CD4 Cell Receptor for HIV", *Nature Med.*, (1996), 2, 230–234; Neurath, A. R., Debnath, A. K., Strick, N. et al., "3-Hydroxyphthaloyl β-Lactoglobulin, I, Optimization of Production and Comparison With Other Compounds Considered for Chemoprophylaxis of Mucosally Transmitted Human Immunodeficiency Virus Type 1", *Antiviral Chem. Chemother.*, (1997), 8, 131–140; Neurath, A. R., Debnath, A. K. Strick N. et al., "3-Hydroxyphthaloyl β-Lactoglobulin, II, Anti-Human Immunodeficiency Virus Type 1 Activity in in vitro Environments Relevant to Prevention of Sexual Transmission of the Virus", *Antiviral Chem. Chemother.*, (1997), 8, 141–148; Neurath, A. R., Strick, N., Li, Y-Y, "3-Hydroxyphthaloyl β-lactoglobulin, III. Antiviral Activity Against Herpesviruses", *Antiviral Chem. Chemother.*, (1998), 9, 177–184; Kokuba, H., Aurelian, L., Neurath, A. R., "3-Hydroxyphthaloyl β-Lactoglobulin, IV, Antiviral Activity in the Mouse Model of Genital Herpevirus Infection", *Antiviral Chem. Chemother.*, (1998), 9, 353–357, by chemical modification of the bovine milk product β-lactoglobulin with 3-hydroxyphthalic anhydride. Possible disadvantages of this antiviral compound has been the lack of activity against bacterial STD pathogens.

c. Viral Infections

Human immunodeficiency viruses ("HIV") have been known as the causative virus for AIDS (Acquired Immunodeficiency Syndrome). The prevalence of AIDS cases is presently increasing at an alarming rate.

Two related retroviruses that can cause AIDS are human immunodeficiency virus type 1 (HIV-1) and type 2 (HIV-2). The genomes of these two viruses are about 50% homologous at the nucleotide level, contain the same complement of genes, and appear to attack and kill the same human cells by the same mechanism.

HIV-1 was identified in 1983. Virtually all AIDS cases in the United States are associated with HIV-1 infection. HIV-2 was isolated in 1986 from West African AIDS patients.

HIV-1 and HIV-2 are retroviruses in which the genetic material is RNA, rather than DNA. The HIV-1 and HIV-2 viruses carry with them a polymerase (reverse transcriptase) that catalyzes transcription of viral RNA into double-helical DNA.

The viral DNA can exist as an unintegrated form in the infected cell or be integrated into the genome of the host cell. As presently understood, the HIV enters the T4 lymphocyte where it loses its outer envelope, releasing viral RNA and reverse transcriptase.

The reverse transcriptase catalyzes synthesis of a complementary DNA strand from the viral RNA template. The DNA helix then inserts into the host genome where it is known as the provirus. The integrated DNA may persist as a latent infection characterized by little or no production of virus or helper/inducer cell death for an indefinite period of time. When the viral DNA is transcribed and translated by the infected lymphocyte, new viral RNA and proteins are produced to form new viruses that bud from the cell membrane and infect other cells.

Attempts to treat AIDS with drugs which inhibit reverse transcriptase such as 3'-azido-3'-deoxythymidine (AZT) have not been met with a desirable degree of success. Moreover, there is a potential for toxicity with the use of anti-viral drugs. Thus there is a need for an effective and safe means to prevent and treat AIDS.

HIV infections are transmitted by means such as contaminated intravenous drug needles and through sexual contact. Sexual transmission is the most frequent (86%) route of adult HIV-1 infections worldwide (*AIDS in the World*, Harvard University Press, Cambridge, Mass., (1992)).

The transmission of HIV by heterosexual sex poses an especially severe problem for women. By the year 2,000, it is estimated that 90% of HIV infections will be acquired via heterosexual intercourse.

The utilization of condoms provides a substantial degree of protection against transmission of HIV and herpesvirus infections during sexual intercourse, but a difficulty arises when condoms are not employed. Moreover, the use of condoms appears to be a culturally and socially unacceptable practice in many countries.

Although men can protect themselves from sexually transmitted HIV and herpesvirus infection by using condoms, women who are sexually active have no similar means. Women can encourage their male sex partners to use a condom, but may not succeed. The female condom, which is just becoming available, is expensive and there is presently no evidence that it prevents sexual transmission of HIV or herpesvirus.

Even maintaining a monogamous sexual relationship is no guarantee of safety, for if a woman's male partner becomes infected, he can pass the virus to her. And as more women are infected, so are more babies.

There is presently frustration in the medical field by the bleak prospect for an effective AIDS vaccine in the near future and the severe limitations of drugs that effectively and safely combat HIV.

Due to the present absence of a prophylactic anti-HIV vaccine and because of limitations of educational programs, other preventive methods have been sought. Spermicides with virucidal properties have been considered for this purpose, but their application is contraindicated by adverse effects (Bird, K. D., "The Use of Spermicide Containing Nonoxynol-9 in the Prevention of HIV Infection", *AIDS*, 5, 791–796 (1991)).

Anti-HIV drugs currently in use or expected to be clinically applied in the near future (Steele, F., "AIDS Drugs Lurch Towards Market", *Nature Medicine*, 1, 285–286 (1995)) are mostly not targeted to the earliest steps in the virus replicative cycle, lead to the emergence of drug resistant mutants, and are expensive, suggesting that their application for wide use in topical chemoprophylaxis is unlikely.

Cells which are the primary targets for sexual and mucosal transmission of HIV, either in the form of free virus or virus-infected cells, have not been fully defined and may be diverse (Miller, C. J. et al., "Genital Mucosal Transmission of Simian Immunodeficiency Virus: Animal Model for Heterosexual Transmission of Human Immunodeficiency Virus", *J. Virol.*, 63, 4277–4284 (1989); Phillips, D. M. and Bourinbaiar, A. S., "Mechanism of HIV Spread from Lymphocytes to Epithelia", *Virology*, 186, 261–273 (1992); Phillips, D. M., Tan, X., Pearce-Pratt, R. and Zacharopoulos, V. R., "An Assay for HIV Infection of Cultured Human Cervix-derived Cells", *J. Virol. Methods*, 52, 1–13 (1995); Ho, J. L. et al., "Neutrophils from Human Immunodeficiency Virus (HIV)-Seronegative Donors Induce HIV Replication from HIV-infected Patients Mononuclear Cells and Cell lines": An In Vitro Model of HIV Transmission Facilitated by *Chlamydia Trachomatis.*," *J. Exp. Med.*, 181, 1493–1505 (1995); and Braathen, L. R. & Mork, C. in "HIV infection of Skin Langerhans Cells", In: *Skin Langerhans (dendritic) cells in virus infections and AIDS* (ed. Becker, Y.) 131–139 (Kluwer Academic Publishers, Boston, (1991)). Such cells include T lymphocytes, monocytes/macrophages and dendritic cells, suggesting that CD4 cell receptors are engaged in the process of virus transmission (Parr, M. B. and Parr, E. L., "Langerhans Cells and T lymphocyte Subsets in the Murine Vagina and Cervix", *Biology of Reproduction*, 44, 491–498 (1991); Pope, M. et al., "Conjugates of Dendritic Cells and Memory T Lymphocytes from Skin Facilitate Productive Infection With HIV-1", *Cell*, 78, 389–398 (1994); and Wira, C. R. and Rossoll, R. M., "Antigen-presenting Cells in the Female Reproductive Tract: Influence of Sex Hormones on Antigen Presentation in the Vagina", *Immunology*, 84, 505–508 (1995)).

Therefore agents blocking HIV-CD4 binding are expected to diminish or prevent virus transmission. Soluble recombinant CD4 cannot be considered for this purpose since high concentrations are required to neutralize the infectivity of primary HIV isolates (Daar, E. S., Li, X. L., Moudgil, T. and Ho, D. D., "High Concentrations of Recombinant Soluble CD4 are Required to Neutralize Primary Human Immunodeficiency Virus Type 1 Isolates", *Proc. Natl. Acad. Sci. U.S.A.*, 87, 6574–6578 (1990), and in the case of SIV, the infectivity is enhanced by CD4 (Werner, A., Winskowsky, G. and Kurth, R., "Soluble CD4 Enhances Simian Immunodeficiency Virus SIVagm Infection", *J. Virol.*, 64, 6252–6256 (1990)). However, anti-CD4 antibodies are expected to prevent virus transmission independently of subtype and variability, but their application would be too costly (Daar et al, supra, Watanabe, M., Boyson, J. E., Lord, C. I. and Letvin, N. L. "Chimpanzees Immunized with Recombinant Soluble CD4 Develop Anti-self CD4 Antibody Responses with Anti-human Immunodeficiency Virus Activity", *Proc. Natl. Acad. Sci. U.S.A.*, 89, 5103–5107 (1992); and Perno, C.-F., Baseler, M. W., Broder, S. and Yarchoan, R., "Infection of Monocytes by Human Immunodeficiency Virus Type 1 Blocked by Inhibitors of CD4-gp120 Binding, Even in the Presence of Enhancing Antibodies", *J. Exp. Med.*, 171, 1043–1056 (1990)).

There is a need for a safe and effective substance that can be inserted into the vagina by a foam, gel, sponge or other form to prevent HIV-1 or HIV-2 from infecting cells in the body. It is hoped that such substance be used by a woman without her partner's knowledge.

Prospects for the near and possibly not so near future to prevent HIV-1 transmission by vaccination do not seem good. A recent report that vaccination with inactivated SIV did not protect African Green monkeys against infection with the homologous virus notwithstanding a strong immune response to SIV does not appear to be encouraging in this respect (Siegel, F., Kurth, R., and Norley, S., (1995), "Neither Whole Inactivated Virus Immunogen nor Passive Immunoglobulin Transfer Protects Against $SIV_{agm}$ Infection in the African Green Monkey Natural Host", *J. AIDS*, 8, 217–226). Considering this problem, emphasis has been put on attempts to build a chemical barrier to HIV-1 transmission (Taylor, (1994), "Building a Chemical Barrier to HIV-1 Transmission", *J. NIH Res.,* 6, 26–27).

The development of topically applied microbicides, expected to prevent sexual (mucosal) transmission of HIV-1, was suggested to need to be "effective against all sexually transmitted diseases and should not be seen, smelled, or felt while in use." It should also be inexpensive and widely available, and $25 million was expected to be devoted to its development in the United States in 1995 (Taylor, (1994) supra). Detergents (nonoxynol-9) as a universal pathogen killer have been selected for clinical trials. However, not surprisingly, this compound proved to be deleterious to the host.

Targeting the chemical barrier to transmission of individual pathogens could perhaps facilitate the development of compounds preventing the transmission of human immunodeficiency viruses. For example, effective blockade of receptors for the viruses might accomplish this goal. This concept may be supported by the finding that immunization of chimpanzees and rhesus monkeys, respectively, with human CD4 which has several amino acid point mutations in comparison with non-human primate CD4 sequences (Fomsgaard, A., Hirsch, V. M., and Johnson, P. R., (1992), "Cloning and Sequences of Primate CD4 molecules: Diversity of the Cellular Receptor for Simian Immunodeficiency Virus/Human Immunodeficiency Virus", *Eur. J. Immunol.,* 22, 2973–2981), developed anti-CD4 antibodies which inhibited HIV-1 and SIV replication (Watanabe, M., Levine, C. G., Shen, L., Fisher, R. A., and Letvin, N. L. (1991), "Immunization of Simian Immunodeficiency Virus-Infected Rhesus Monkeys with Soluble Human CD4 Elicits an Antiviral Response," *Proc. Natl. Acad. Sci. USA,* 88, 4616–4620. Watanabe, M., Chen, Z. W., Tsubota, H., Lord, C. I., Levine, C. G., and Letvin, N. L., (1991), "Soluble Human CD4 Elicits an Antibody Response in Rhesus Monkeys that Inhibits Simian Immunodeficiency Virus Replication", *Proc. Natl. Acad. Sci. USA,* 88, 120–124; and Watanabe, M., Boyson, J. E., Lord, C. I., and Letvin, N. L., (1992), "Chimpanzees Immunized with Recombinant Soluble CD4 Develop Anti-self CD4 Antibody Responses with Anti-human Immunodeficiency Virus Activity", *Proc. Natl. Acad. Sci. USA,* 89, 5103–5107).

Herpesviruses include the following viruses isolated from humans:
(1) herpes simplex virus 1 ("HSV-1")
(2) herpes simplex virus 2 ("HSV-2")
(3) human cytomegalovirus ("HCMV")
(4) varicella-zoster virus ("VZV")
(5) Epstein-Barr virus ("EBV")
(6) human herpesvirus 6 ("HHV6")
(7) herpes simplex virus 7 ("HSV-7")
(8) herpes simplex virus 8 ("HSV-8")

Herpesviruses have also been isolated from horses, cattle, pigs (pseudorabies virus ("PSV") and porcine cytomegalovirus), chickens (infectious larygotracheitis), chimpanzees, birds (Marck's disease herpesvirus 1 and 2), turkeys and fish (see "Herpesviridae: A Brief Introduction", *Virology,* Second Edition, edited by B. N. Fields, Chapter 64, 1787 (1990)).

Herpes simplex viral ("HSV") infection is generally a recurrent viral infection characterized by the appearance on the skin or mucous membranes of single or multiple clusters of small vesicles, filled with clear fluid, on slightly raised inflammatory bases.

The herpes simplex virus is a relatively large-sized virus. HSV-2 commonly causes herpes labialis. HSV-2 is usually, though not always, recoverable from genital lesions. Ordinarily, HSV-2 is transmitted venereally.

At least 20% of people in the United States have been infected with herpesvirus type 2 (HSV-2), which is usually transmitted sexually and can cause recurrent genital ulcers (Fleming, D. T., McQuillan, G. M., Johnson, R. E. et al., "Herpes simplex virus type 2 in the United States, 1976 to 1994", *N. Eng. J. Med.,* (1997), 337:1105–1111; Arvin, A. M., Prober, C. G., "Herpes Simplex Virus Type 2—A Persistent Problem", *N. Engl. J. Med.,* (1997), 337:1158–1159). The prevalence of HSV-2 infections is even higher in some developing countries (Nahmias, A. J., Lee, F. K., Beckman-Nahmias, S., "Sero-epidemiologial and Sociological Patterns of Herpes Simplex Virus Infection in the World", *Scand. J. Infect. Dis.,* (1990), Suppl. 69:19–36). Although the infection is treatable by antiviral drugs, efficacious long-term suppression of genital herpes is expensive (Engel, J. P., "Long-term Suppression of Genital Herpes", *JAMA,* (1998), 280:928–929). The probability of further spread of the virus by untreated people and asymptomatic carriers not receiving antiviral therapy is extremely high, considering the high prevalence of infections. Other herpesviruses, including cytomegalovirus (Krieger, J. N., Coombs, R. W., Collier, A. C. et al., "Seminal Shedding of Human Immunodeficiency Virus Type 1 and Human Cytomegalovirus: Evidence For Different Immunologic Controls", *J. Infect. Dis.,* (1995), 171:1018–1022; van der Meer, J. T. M., Drew, W. L., Bowden R. A. et al., "Summary of the International Consensus Symposium on Advances in the Diagnosis, Treatment and Prophylaxis of Cytomegalovirus Infection", *Antiviral Res.,* (1996), 32:119–140) (HCMV), herpesvirus 6 (Leach, C. T., Newton, E. R., McParlin, S. et al., "Human Herpesvirus 6 Infection of the Female Genital Tract", *J. Infect. Dis.,* (1994), 169:1281–1283), and herpesvirus 8 (Howard, M. R., Whitby, D., Bahadur, G. et al., "Detection of Human Herpesvirus 8 DNA in Semen from HIV-infected Individuals But Not Healthy Semen Donors", *AIDS,* (1997), 11:F15–F19), the causative agent of Kaposi's sarcoma, are also transmitted sexually.

The time of initial herpes simplex virus infection is usually obscure except in the uncommon primary systemic infection occurring in infants and is characterized by generalized cutaneous and mucous membrane lesions accompanied by severe constitutional symptoms. Localized infections ordinarily appear in childhood, but may be delayed until adult life. It is presumed that the herpes simplex virus remains dormant in the skin and that herpetic eruptions are precipitated by overexposure to sunlight, febrile illnesses, or physical or emotional stress; also, certain foods and drugs have been implicated. In many instances, the trigger mechanism remains undetected.

The lesions caused by herpes simplex virus may appear anywhere on the skin or on mucous membranes, but are most frequent on the face, especially around the mouth or on the lips, conjunctiva and cornea, or the genitals. The appearance of small tense vesicles on an erythematous base follows a short prodromal period of tingling discomfort or itching. Single clusters may vary from 0.5 to 1.5 cm in size, but several groups may coalesce. Herpes simplex on skin tensely attached to underlying structures (for example, the nose, ears or fingers) may be painful. The vesicles may persist for a few days, then begin to dry, forming a thin yellowish crust. Healing usually occurs within 10 days after onset. In moist body areas, healing may be slower, with secondary inflammation. Healing of individual herpetic lesions is usually complete, but recurrent lesions at the same site may result in atrophy and scarring.

In females infected with HSV-2, there may be no skin lesions, the infection may remain entirely within the vagina.

The cervix is frequently involved, and there is increasing evidence that this may be a factor in the development of carcinoma of the cervix.

Corneal lesions commonly consist of a recurrent herpetic keratitis, manifest by an irregular dendritic ulcer on the superficial layers. Scarring and subsequent impairment of vision may follow.

Gingivostomatitis and vulvovaginitis may occur as a result of herpes infection in infants or young children. Symptoms include irritability, anorexia, fever, inflammation, and whitish plaques and ulcers of the mouth. Particularly in infants, though sometimes in older children, primary infections may cause extensive organ involvement and fatal viremia.

In women who have an attack of HSV-2 late in pregnancy, the infection may be transmitted to the fetus, with the development of severe viremia. Herpes simplex virus may also produce fatal encephalitis.

Kaposi's varicelliform eruption (eczema herpeticum) is a potentially fatal complication of infantile or adult atopic eczema. Exposure of patients with extensive atopic dermatitis to persons with active herpes simplex should be avoided.

No local or systemic chemotherapeutic agent has been demonstrated to be effective for treating herpes simplex virus with the possible exception of topical idoxuridine (IDU) in superficial herpetic keratitis. Reports on this compound in cutaneous herpes are conflicting. Other drugs which have been employed to treat HSV include trifluorothymidine, vidarabine (adenine arabinoside, ara-A), acyclovir, and other inhibitors of viral DNA synthesis may be effective in herpetic keratitis. These drugs inhibit herpes simplex virus replication and may suppress clinical manifestations. However, the herpes simplex virus remains latent in the sensory ganglia, and the rate of relapse is similar in drug-treated and untreated individuals. Moreover, some drug-resistant herpes virus strains have emerged.

Diseases caused by varicella-zoster virus (human herpesvirus 3) include varicella (chickenpox) and zoster (shingles).

Cytomegalovirus (human herpesvirus 5) is responsible for cytomegalic inclusion disease in infants. There is presently no specific treatment for treating patients infected with cytomegalovirus.

Epstein-Barr virus (human herpesvirus 4) is the causative agent of infectious mononucleosis and has been associated with Burkitt's lymphoma and nasopharyngeal carcinoma.

Animal herpesviruses which may pose a problem for humans include B virus (herpesvirus of Old World Monkeys) and Marmoset herpesvirus (herpesvirus of New World Monkeys).

In searching for inexpensive antiviral compounds which could be applied topically to decrease the frequency of sexual transmission of the human immunodeficiency virus type 1 (HIV-1) and herpesviruses (HSV), applicants decided against all odds to screen excipients for anti-HIV-1 activity and discovered the present invention which involves the administration of cellulose acetate phthalate ("CAP") or hydroxypropyl methylcellulose phthalate ("HPMCP").

d. Sexually Transmitted Diseases of Bacterial Origin

Curable sexually transmitted diseases (STDs) of bacterial origin are the most common worldwide cause of illness with significant health, social and economic consequences. They can lead to long-term, serious complications and sequelae. The estimated annual (1995) worldwide incidence of four major curable STDs, namely syphillis, gonorrhea (*Neisseria gonorrhoeae*), chlamydia and trichomoniasis, was about 330 million (Gerbase, A. C., Rowley, J. T., Heymann, D. H. L. et al., "Global Prevalence and Incidence Estimates of Selected Curable STDs", *Sex. Transm. Inf.,* (1998), 74 (Suppl. 1): S12–S16). Another treatable STD, chancroid, a genital ulcerative disease caused by *Haemophilus ducreyi,* is common in developing countries in Africa, Asia and Latin America, where incidence may exceed that of syphillis (Trees, D. L., Morse, S. A., "Chancroid and *Haemophilus ducreyi:* An Update", *Clin. Microb. Rev.,* (1995), 8:357–375). The proposed control measures for these STDs include the following: surveillance, laboratory diagnosis, syndromic management, data monitoring, treatment with antibacterial agents, partner notification and development of vaccines (Rao, P., Mohamedali, F. Y., Temmerman, M. et al., "Systematic Analysis of STD Control: an Operational Model", *Sex. Transm. Inf.,* (1998), 74 (Suppl 1): S17–S22; Dallabetta, G. A., Gerbase, A. C., Holmes, K. K., "Problems, Solutions, and Challenges in Syndromic Management of Sexually Transmitted Diseases", *Sex. Transm. Inf.,* (1998), 74 (Suppl 1): S1–S11; Burstein, G. R., Gaydos, C. A., Diener-West M., "Incident Chlamydia Trachomatis Infections Among Inner-city Adolescent Females", *JAMA,* (1998), 280:521–526).

There has thus heretofore been desired the development of a topical microbicide from inexpensive, widely available resources, with broad antiviral and antibacterial activities.

SUMMARY OF THE INVENTION

An object of the present invention is to provide a safe and relatively inexpensive method to decrease the frequency of transmission of human immunodeficiency virus and herpesvirus viral infections, particularly those which are sexually transmitted.

A further object of the present invention is to provide a composition for decreasing the frequency of transmission of human immunodeficiency virus and herpesvirus.

Another object of the present invention is to provide methods for treating and preventing sexually transmitted bacterial infections.

The above objects, along with all objects, aims and disadvantages, are achieved by the present invention.

The present invention concerns a method for decreasing the frequency of transmission and, particularly, preventing the transmission of human immunodeficiency virus or herpesvirus by administering to a human an effective anti-human immunodeficiency virus or anti-herpesvirus amount of at least one cellulose phthalate selected from the group consisting of acetate phthalate (CAP) and hydroxypropyl methylcellulose phthalate (HPMCP) either alone, or in combination with a pharmaceutically acceptable carrier or diluent.

The present invention also concerns a pharmaceutical composition for decreasing the frequency of transmission of human immunodeficiency virus or herpesvirus comprising an effective anti-immunodeficiency virus amount or effective anti-herpesvirus amount of at least one cellulose phthalate selected from the group consisting of cellulose acetate phthalate and hydroxypropyl methylcellulose phthalate in combination with a pharmaceutically acceptable carrier or diluent.

The present invention further relates to a method for preventing the transmission of a sexually transmitted bacterial infection in a human, or treating a human infected with a sexually transmitted bacterial infection comprising administering to the human an effective anti-bacterial amount of at least one cellulose phthalate selected from the group consisting of acetate phthalate (CAP) and hydroxypropyl methylcellulose phthalate (HPMCP) either alone, or in combination with a pharmaceutically acceptable carrier or diluent.

The present invention also concerns a pharmaceutical composition for preventing the transmission of or for treating a sexually transmitted bacterial infection comprising an effective anti-bacterial amount of at least one cellulose phthalate selected from the group consisting of cellulose acetate phthalate and hydroxypropyl methylcellulose phthalate in combination with a pharmaceutically acceptable carrier or diluent.

The present invention is also directed to the aforesaid methods and pharmaceutical compositions, wherein the cellulose phthalate (CAP and/or HPMCP) is provided in the form of a suspension and preferably in a micronized form. Further, such suspension may include a water miscible, essentially anhydrous, non-solvent for CAP or HPMCP, such as glycerol.

BRIEF DESCRIPTION OF THE DRAWINGS

FIG. 1 thus shows the inhibitory effect of cellulose acetate phthalate ("CAP") on HSV-1 and HSV-2.

FIG. 3 shows the disintegration of purified HIV-1 by treatment with an "AQUATERIC"-glycerol formulation ("CAP formulation I") with or without polyvinyl pyrrolidone (PVP) and Crospovidone for 5 minutes at 37° C., as measured by the release of the nucleocapsid antigen p24.

FIG. 4 shows the inactivation of HIV-1 infectivity by treatment with an "AQUATERIC"-glycerol formulation containing 286 mg/ml of "AQUATERIC" for 5 minutes at 37° C., as determined by production of the nucleocapsid antigen p24 by infected cells as measured by ELISA.

FIG. 5 shows the inactivation of HSV-1 and HSV-2 by a suspension of "AQUATERIC" in glycerol. Virus preparations were mixed 1:1 with a suspension of "AQUATERIC" in glycerol for 5 minutes at 37° C.

FIG. 6 shows the inactivation of HSV-1 and HSV-2 by an "AQUATERIC"-glycerol formulation with PVP and Crospovidone.

DETAILED DESCRIPTION OF THE INVENTION

Figure 1:
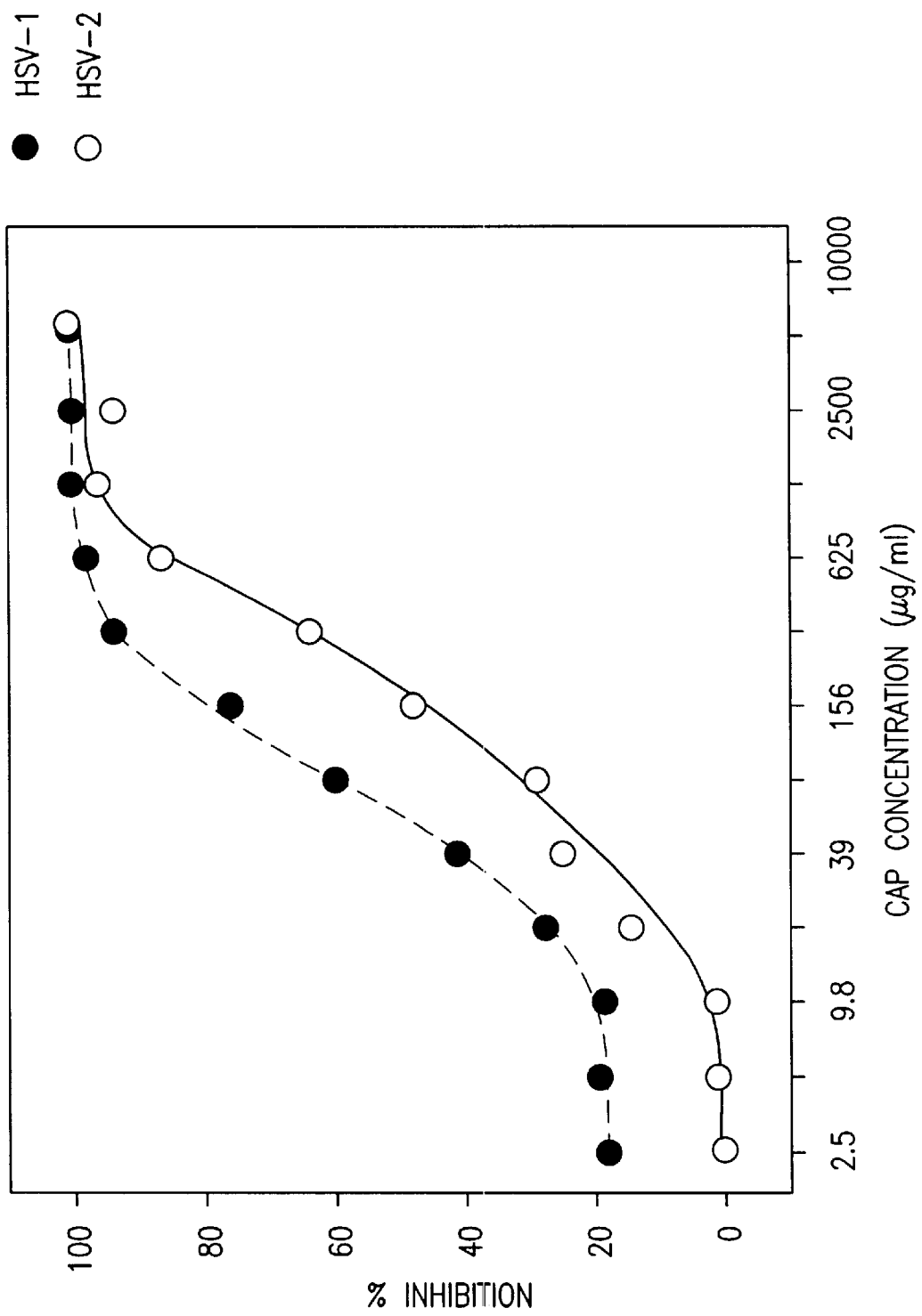
FIG. 1 is a graph of % inhibition vs. cellulose acetate phthalate ("CAP") concentration, for HSV-1 and HSV-2.

The present invention involves the use of cellulose acetate phthalate (CAP) and/or hydroxypropyl methylcellulose phthalate (HPMCP) to prevent the transmission of viral infections and to prevent or treat sexually transmitted bacterial infections.

Some of the properties of CAP as described in the *Handbook of Pharmaceutical Excipients* are summarized as follows:

Non proprietary Names:
BP: Cellacephate
PhEur: Cellulosi acetas phthalas
USPNF: Cellulose acetate phthalate
Synonyms:
Acetyl phthalyl cellulose; CAP; cellacefate; cellulose acetate hydrogen 1,2-benzenedicarboxylate; cellulose acetate hydrogen phthalate; cellulose acetate monophthalate; cellulose acetophthalate; cellulose acetylphthalate.
Chemical Name and CAS Registry Number:
Cellulose, acetate, 1,2-benzenedicarboxylate [9004-38-0]
Cellulose acetate phthalate is a cellulose in which about half the hydroxyl groups are acetylated and about a quarter are esterified, with one of the two acid groups being phthalic acid. The other acid group is free. See the structural formula below.

Structural Formula:

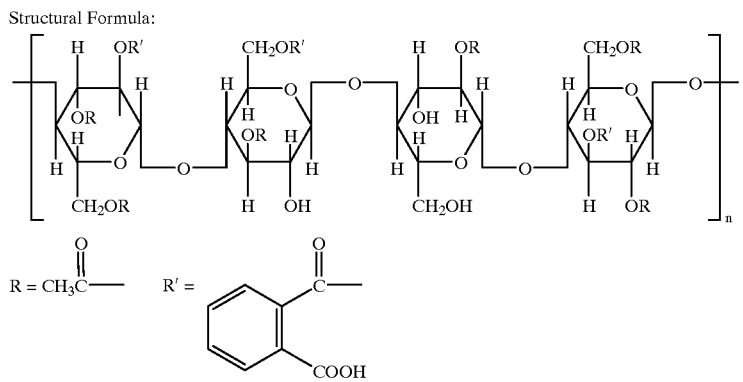

Functional Category:
Coating agent.
Applications in Pharmaceutical Formulation or Technology:
Cellulose acetate phthalate has heretofore been used as an enteric film coating material, or as a matrix binder, for tablets and capsules (Spitael, J., Kinget, R., Naessens, K., "Dissolution Rate of Cellulose Acetate Phthalate and Br önsted Catalysis Law", *Pharm. Ind.,* (1980), 42:846–849; Takenaka, H., Kawashima, Y., Lin, S-Y., "Preparation of Enteric-Coated Microcapsules for Tableting by Spray-Drying Technique and in vitro Simulation of Drug Release from the Tablet in GI Tract", *J. Pharm., Sci.,* (1980), 69:1388–1392; Stricker, H., Kulke, H., "Rate of Disintegration and Passage of Enteric-Coated Tablets in Gastrointestinal Tract", *Pharm. Ind.,* (1981), 43:1018–1021; Takenaka, H., Kawashima, Y., Lin, S-Y, "Polymorphism of Spray-Dried Microencapsulated Sulfamethoxazole with Cellulose Acetate Phthalate and Colloidal Silica Montmorillonite, or Talc", *J. Pharm. Sci.,* (1981), 70:1256–1260; Maharaj, I., Nairn, J. G., Campbell J. B., "Simple Rapid method for the Preparation of Enteric-Coated Microspheres", *J. Pharm. Sci.,* (1984), 73:39–42; Beyger, J. W., Nairn, J. G., "Some Factors Affecting the Microencapsulation of Pharmaceuticals with Cellulose Acetate Phthalate", *J. Pharm. Sci.,* (1986), 75-573–578; Lin, S-Y, Kawashima, Y., "Drug Release from Tablets Containing Cellulose Acetate Phthalate as an Additive or Enteric-Coating Material", *Pharm. Res.,* (1987), 4:70–74; Thoma, K. Hekenmüller, H., "Effect of Film Formers and Plasticizers on Stability of Resistance and Disintegration Behaviour, Part 4: Pharmaceutical-Technological and Analytical Studies of Gastric Juice Resistant Commercial Preparations", *Pharmazie,* (1987), 42:837–841).

Such coatings resist prolonged contact with the strongly acidic gastric fluid, but soften and swell in the mildly acidic or neutral intestinal environment.

Cellulose acetate phthalate, when heretofore used as an adjuvant, was commonly applied to solid dosage forms either by coating from organic or aqueous solvent systems, or by direct compression. Concentrations used were 0.5 to 9.0% of the core weight. The addition of plasticizers improves the water resistance of this coating material, and such plasticized films are more effective than when cellulose acetate phthalate is used alone as an adjuvant. Cellulose acetate phthalate is compatible with the following plasticizers: acetylated monoglyceride; butyl phthalylbutyl glycolate; dibutyl tartrate; diethyl phthalate; dimethyl phthalate; ethyl phthalyethyl glycolate; glycerin; propylene glycol; triacetin; triacetin citrate and tripropionin. Cellulose acetate phthalate has also been used heretofore in combination with other coating agents to control drug release, e.g., ethylcellulose.

Description:

Cellulose acetate phthalate is a hygroscopic, white, free-flowing powder or colorless flakes. It is tasteless and odorless, or may have a slight odor of acetic acid.

Pharmacopeial Specifications:

| Test | PhEur 1984 | USPNF XVII (Suppl 2) |
|---|---|---|
| Identification | + | + |
| Appearance of solution | + | – |
| Appearance of a film | + | – |
| Solubility of a film | + | – |
| Viscosity at 25° C. | – | 45–90 cP |
| Water | ≦5.0% | ≦5.0% |
| Residue on ignition | – | ≦0.1% |
| Sulfated ash | ≦0.1% | – |
| Free acid | ≦3.0% | ≦6.0% |
| Heavy metals | ≦10 ppm | – |
| Phthalyl content | 30.0–40.0% | 30.0–36.0% |
| Acetyl content | 17.0–26.0% | 21.5–26.0% |

Typical Properties:

Hygroscopicity: cellulose acetate phthalate is hygroscopic and precautions are necessary to avoid excessive absorption of moisture (Callahan, J. C., Cleary, G. W., Elefant, M., Kaplan, G., Kensler, T., Nash, R. A., "Equilibrium Moisture Content of Pharmaceutical Excipients", *Drug Dev. Ind. Pharm.,* (1982), 8:355–369).

Melting point: 192° C. Glass transition temperature is 160–170° C. (Sakellariou, P., Rowe, R. C., White, E. F. T., "The Thermomechanical Properties and Glass Transition Temperatures of Some Cellulose Derivatives used in Film Coating", *Int. J. Pharmaceutics,* (1985), 27:267–277).

Solubility: practically insoluble in alcohols, chlorinated hydrocarbons, hydrocarbons, and water; soluble in cyclic ethers, esters, ether alcohols, ketones and certain solvent mixtures. Also soluble in certain buffered aqueous solutions at greater than pH 6. The following list shows some of the solvents and solvent mixtures in which cellulose acetate phthalate has a solubility of 1 in 10 parts or more.

Acetone
Acetone: Ethanol (1:1)
Acetone: Methanol (1:1/1:3)
Acetone: Methylene chloride (1:1/1:3)
Acetone: Water (97:3)
Benzene: Methanol (1:1)
Diacetone alcohol
Dioxane
Ethoxyethyl acetate
Ethyl acetate: Ethanol (1:1)
Ethyl acetate: Propan-2-ol (1:1/1:3)
Ethylene glycol monoacetate
Ethyl lactate
Methoxyethyl acetate
β-Methoxyethylene alcohol
Methyl acetate
Methylene chloride: Ethanol (3:1)
Methyl ethyl ketone Viscosity (dynamic): 50–90 mPas (50–90 cP) for a 15% w/w solution in acetone with a moisture content of 0.4%. This is a good coating solution with a honey-like consistency, but the viscosity is influenced by the purity of the solvent.

Stability and Storage Conditions:

Cellulose acetate phthalate hydrolyzes slowly under prolonged adverse conditions, such as high temperature and humidity, with a resultant increase in free acid content, viscosity and odor of acetic acid. If its moisture content is above about 6% w/w, fairly rapid hydrolysis occurs. However, cellulose acetate phthalate is stable if stored in a well-closed container in a cool, dry place.

Incompatibilities:

Cellulose acetate phthalate is incompatible with ferrous sulfate, ferric chloride, silver nitrate, sodium citrate, aluminum sulfate calcium chloride, mercuric chloride, barium nitrate, basic lead acetate, and strong oxidizing agents such as strong alkalis and acids. It should be noted that one carboxylic acid group of the phthalic acid moiety remains unesterified and free for interactions. Accordingly, incompatibility with acid sensitive drugs may occur (Rawlins E. A., editor, "Bentley's Textbook of Pharmaceutics", London: Baillière, Tindall and Cox, (1977), 291).

Method of Manufacture:

Cellulose acetate phthalate is produced by reacting the partial acetate ester of cellulose with phthalic anhydride in the presence of a tertiary organic base, such as pyridine.

Safety:

Cellulose acetate phthalate is widely used in oral pharmaceutical products and is generally regarded as a nontoxic material, free of adverse effects.

Results of long-term feeding studies with cellulose acetate phthalate, in rats and dogs, have indicated a low oral toxicity. Rats survived daily feedings of up to 30% in the diet for up to one year without showing a depression in growth. Dogs fed 16 g daily in the diet for one year also remained normal (Hodge, H. C., "The Chronic Toxicity of Cellulose Acetate Phthate in Rats and Dogs", *J. Pharmacol.*, 80, 250–255, (1944)).

Regulatory Status:

Included in the FDA Inactive Ingredients Guide (oral capsules and tablets). Included in nonparenteral medicines licensed in the United Kingdom.

Pharmacopeias: Aust, Br, Braz, Cz, Eur, Fr, Ger, Gr, Hung, Ind, It, Jpn, Mex, Neth, Nord, Port, Swiss and USPNF.

Some of the properties of HPMCP, described in the *Handbook of Pharmaceutical Excipients* are summarized as follows:

Non proprietary Names: BP: Hypromellose phthalate; PhEur: Methylhydroxypropylcellulosi phthalas and USPNF: Hydroxypropyl methylcellulose phthalate.

Synonyms: Cellulose phthalate hydroxypropyl methyl ether; HPMCP; 2-hydroxypropyl methylcellulose phthalate; methylhydroxypropylcellulose phthalate.

Chemical Name and CAS Registry Number: Cellulose, hydrogen 1,2-benzenedicarboxylate, 2-hydroxypropyl methyl ether [9050-31-1]

Structural Formula:

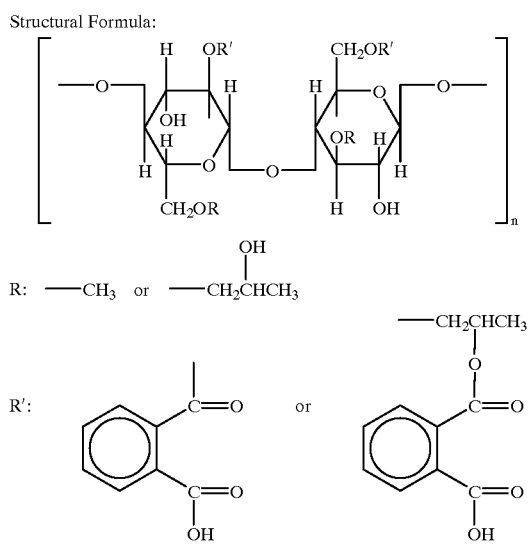

Functional Category: Coating agent.

Applications in Pharmaceutical Formulations or Technology

Hydroxypropyl methylcellulose phthalate has heretofore been widely used in oral pharmaceutical formulations as an enteric coating material for tablets or granules (Ehrhardt, L., Patt, L., Schindler, E., "Optimization of Film Coating Systems", *Pharm. Ind.*, (1973), 35:719–722; Delporte, J. P., Jaminet, F., "Influence of Formulation of Enteric-Coated Tablets on the Bioavailability of the Drug", *J. Pharm. Belg.*, (1976), 31-263–276; Patt, L., Hartmann V., "Solvent Residues in Film Forming Agents", *Pharm. Ind.*, (1976), 38:902–906; Stafford, J. W., "Enteric Film Coating Using Completely Aqueous Dissolved Hydroxypropyl Methylcellulose Phthalate Spray Solutions", Drug. Dey Ind. Pharm., (1982), 8:513–530; Thoma, K., Heckenmüller, H., Oschmann, R., "Resistance and Disintegration Behaviour of Gastric Juice Resistant Drugs", *Pharmazie*, (1987), 42:832–836; Thoma, K., Heckenmüller, H., Oschmann, R., "Impact of Film Formers and Plasticizers on Stability of Resistance and Disintegration Behaviour", *Pharmazie*, (1987), 42:837–841).

Hydroxypropyl methylcellulose phthalate is insoluble in gastric fluid, but will swell and dissolve rapidly in the upper intestine. Generally, concentrations of 5–10% of hydroxypropyl methylcellulose phthalate were employed with the material being dissolved in either a dichloromethane:ethanol (50:50) or an ethanol:water (80:20) solvent mixture. Hydroxypropyl methylcellulose phthalate can normally be applied to tablets and granules without the addition of a plasticizer or other film formers, using established coating techniques (Rowe, R. C., "Molecular Weight Studies on the Hydroxypropyl Methylcellulose Phthalate (HP55)", *Acta. Pharm. Technol.*, (1982), 28(2):127–130. However, the addition of a small amount of plasticizer or water can avoid film cracking problems; many commonly used plasticizers such as diacetin, triacetin, diethyl and dibutyl phthalate, castor oil, acetyl monoglyceride and polyethylene glycols are compatible with hydroxypropyl methylcellulose phthalate. Tablets coated with hydroxypropyl methylcellulose phthalate disintegrate more rapidly than tablets coated with cellulose acetate phthalate.

Hydroxypropyl methylcellulose phthalate can be applied to tablet surfaces using a dispersion of the micronized hydroxypropyl methylcellulose phthalate powder in an aqueous dispersion of a suitable plasticizer such as triacetin, triethyl citrate or diethyl tartrate along with a wetting agent (Muhammad, N. A., Boisvert, W., Harris, M. R., Weiss, J., "Evaluation of Hydroxypropyl Methylcellulose Phthalate 50 as Film Forming Polymer from Aqueous Dispersion Systems", *Drug Dev. Ind. Pharm.*, (1992), 18:1787–1797).

Hydroxypropyl methylcellulose phthalate may be used alone or in combination with other soluble or insoluble binders in the preparation of granules with sustained drug release properties; the release rate is pH dependent. Since hydroxypropyl methylcellulose phthalate is tasteless and insoluble in saliva, it can be used as a coating to mask the unpleasant taste of some tablet formulations.

Description:

Hydroxypropyl methylcellulose phthalate occurs as white to slightly off-white colored free-flowing flakes or as a granular powder. It is odorless or with a slightly acidic odor, and a barely detectable taste.

Typical Properties:

Melting point: 150° C.

Solubility: practically insoluble in ethanol and water; very slightly soluble in acetone, and toluene; soluble in aqueous alkalis, a mixture of equal volumes of acetone and methanol, and in a mixture of equal volumes of dichloromethane and methanol.

Stability and Storage Conditions:

Hydroxypropyl methylcellulose phthalate is chemically and physically stable at ambient temperature and humidity for 3–4 years, and for 2 to 3 months at 40° C. and 75% relative humidity (Shin-Etsu Chemical Co., Ltd., Technical Literature: Hydroxypropyl Methylcelluose Phthalate, (1993). Hydroxypropyl methylcellulose phthalate is stable on exposure to UV light for up to 3 months at 25° C. and 70% relative humidity (Shin-Etsu Chemical Co., Ltd., Technical Literature: Hydroxypropyl Methylcellulose Phthalate, (1993). In general, hydroxypropyl methylcellulose phthalate is more stable than cellulose acetate phthalate. At ambient storage conditions, hydroxypropyl methylcellulose phthalate is not susceptible to microbial attack.

Incompatibilities:

Incompatible with strong oxidizing agents. Splitting of film coatings has been reported rarely, most notably with coated tablets which contain microcrystalline cellulose and calcium carboxymethylcellulose. Film splitting has also occurred when a mixture of acetone: propan-2-ol or dichloromethane: propan-2-ol has been used as a coating solvent, or when coatings have been applied in conditions of low temperature and humidity. However, film splitting may be avoided by careful selection of the coating solvent used, by using a higher molecular weight grade of polymer (Rowe, R. C., "Molecular Weight Studies on the Hydroxypropyl Methylcellulose Phthalate (HP55), *Acta. Pharm. Technol.,* (1982), 28(2):127–130), or by the addition of a plasticizer, such as acetyl monoglyceride or triacetin. The addition of more than about 10% titanium dioxide to a coating solution of hydroxypropyl methylcellulose phthalate, that is used to produce a colored film coating, may result in coatings with decreased elasticity and gastric fluid resistance (Shin-Etsu Chemical Co., Ltd., Technical Literature: Hydroxypropyl Methylcellulose Phthalate, (1993)).

Method of Manufacture:

Hydroxypropyl methylcellulose acetate phthalate is prepared by the esterification of hydroxypropyl methylcellulose with phthalic anhydride. The degree of methoxy and phthalyl substitution determines the properties of the polymer and in particular the pH at which it dissolves in aqueous media.

Safety:

Hydroxypropyl methylcellulose phthalate has been heretofore widely used, primarily as an enteric coating agent, in oral pharmaceutical formulations. Chronic and acute animal feeding studies on several different species have shown no evidence or teratogenicity or toxicity associated with hydroxypropyl methylcellulose phthalate (Kitagawa, H., Kawana, H., Satoh, T., Fukuda, Y., "Acute and Subacute Toxicities of Hydroxypropyl Methylcellulose Phthalate", *Pharmacometrics,* (1970), 4(6):1017–1025; Kitagawa, H., Satoh, T., Yokoshima, T., Nanbo, T., "Absorption, Distribution and Excretion of Hydroxypropyl Methylcellulose Phthalate in the Rat", *Pharmacometrics,* (1971), 5(1):1–4; Ito, R., Toida, S., "Studies on the Teratogenicity of a New Enteric Coating Material, Hydroxypropyl Methylcellulose Phthalate (HPMCP) in Rats and Mice", *J. Med. Soc. Toho-Univ.,* (1972), 19(5):453–461; Kitagawa, H., Yano, H., Fukuda, Y., "Chronic Toxicity of Hydroxypropylmethylcellulose Phthalate in Rats", *Pharmacometrics,* (1973), 7(5) ;689–701; Kitagawa, H., Yokoshima, T., Nanbo, T., Hasegawa, M., "Absorption, Distribution, Excretion and Metabolism of $^{14}$C-hydroxypropyl Methylcellulose Phthalate", *Pharmacometrics,* (1974), 8(8):1123–1132. Hydroxypropyl methylcellulose phthalate is generally regarded as a nonirritant and nontoxic material.

$LD_{50}$ (rat, oral): >15 g/kg (Kitagawa et al., *Pharmacometrics,* (1970), 4(6):1017–1025).

Regulatory Status: included in the FDA Inactive Ingredients Guide (oral capsules and tablets) and included in non-parenteral medicines licensed in the United Kingdom.

Pharmacopeias: Br, Eur, Fr, Gr, It, Jpn, Neth, Port, Swiss and USPNF.

Related Substances: cellulose acetate phthalate; Hydroxypropyl Methylcellulose.

A particularly preferred composition for topically administering to a human in accordance with the present invention comprises a micronized preparation containing CAP or micronized HPMCP, a poloxamer and distilled acetylated monoglycerides (a mixture of micronized CAP, poloxamer and acetylated monoglycerides is sold by the FMC Corporation under the trade name "AQUATERIC") suspended in glycerol. A poloxamer is a nonionic polyoxyethylene-polyoxypropylene copolymer. Squalane (2,6,10,15,19,23-hexamethyltetracosane) can be used instead of glycerol.

A chemical name for a poloxamer is α-hydro-ω-hydroxypoly(oxyethylene) poly(oxypropylene) poly(oxyethylene) block copolymer. The poloxamer polyols are a series of closely related block copolymers of ethylene oxide and propylene oxide conforming to the following formula:

$$HO(C_2H_4O)_a(C_3H_6O)_b(C_2H_4O)_aH.$$

| The following is a list of grades of poloxamers (USPNF XVII): | | | | |
|---|---|---|---|---|
| Poloxamer | Physical Form | a | b | Average Molecular Weight |
| 124 | Liquid | 12 | 20 | 2,090 to 2,360 |
| 188 | Solid | 80 | 27 | 7,680 to 9,510 |
| 237 | Solid | 64 | 37 | 6,840 to 8,830 |
| 338 | Solid | 141 | 44 | 12,700 to 17,400 |
| 407 | Solid | 101 | 56 | 9,840 to 14,600 |

To prevent separation from the glycerol of the microsuspension containing the CAP or HPMCP, the poloxamer and the distilled acetylated monoglycerides, it is preferred to add polyvinylpyrrolidone ("PVP") and a 1-ethenyl-2-pyrrolidinone homopolymer (Crospovidone) (Polyplasdone) $(C_6H_9NO)_n$, molecular weight>1,000,000) (water insoluble synthetic cross-linked homopolymer of N-vinyl-2-pyrrolidinone).

The term micronized used herein refers to particles having a particle size of less than 35 microns, preferably less than 15 microns, more preferably less than 10 microns and most preferably less than 5 microns.

In the composition described herein which includes glycerol, the glycerol may be replaced with a saline solution or water, so long as the composition is stored at ≦25° C.

CAP is commonly used as an enteric film coating material or as a matrix binder for tablets and capsules. Its safety has been extensively studied and it has been shown to be free of adverse effects. Vaginal irritation tests in the rabbit model further confirmed its safety. CAP is a high molecular weight compound ($M_w$ is approximately 60,000), indicating that if topically applied, it will not spread systemically. The likelihood of CAP spreading beyond the site of application has been further decreased by using it in a micronized form.

Formulations of CAP were discovered by the applicants to be active against HIV-1, herpesviruses, HSV-1, and HSV-2, cytomegalovirus, *Chlamydia trochomatis, garderella, Neisseria gonorrhoeae, Haemophilus ducreyi,* and *Trichomonas vaginalis.*

On the other hand, the CAP formulations did not affect the viability of Lactobacilli which are essential components of the natural vaginal flora imortant for resistance against some STD pathogens (Hawes, S. E., Hillier, S. L., Benedetti, J. et al., "Hydrogen Peroxide-Producing Lactobacilli and Acquisition of Vaginal Infections", *J. Infect. Dis.,* (1995), 172, 756–763).

Results indicated that the formulation did not affect the infectivity of papillomaviruses, another STD pathogen, involved in cervical cancer (Franco, E. L, Villa, L. L., Ruiz, A. et al., "Transmission of Cervical Human Papillomavirus Infection by Sexual Activity: Differences Between Low and High Oncogenic Risk Types", *J. Infect. Dis.,* (1995), 172, 756–763; Bosch, F. X., Munoz, N., de Sanjose, S. et al., "Importance of Human Papillomavirus Endemicity in the Incidence of Cervical Cancer: An Extension of the Hypothesis on Sexual Behavior", *Cancer Epidemiol. Biomarkers & Prev.*, (1994), 3, 375–379).

Without wishing to be bound by any particular theory of operability, it is considered that the anti-viral and anti-bacterial activity of CAD may be atributable to the hydrophobic nature of the phthalate residues on the CAP polymer for its activity appears to be important against pathogens of sexually transmitted diseases, since many other cellulose derivatives tested lacked both anti-HIV-1 and anti-herpesvirus activity.

A preferred composition for administration in the present invention can be made as follows: dissolve PVP in glycerol, then add cross-linked 1-ethenyl-2-pyrrolidinone homopolymer (Crospovidone) (Crospovidone is cross-linked povidone) and a composition comprising micronized CAP and poloxamer and acetylated monoglycerides. The PVP and cross-linked 1-ethenyl-2-pyrrolidinone homopolymer would be in concentrations sufficient to stabilize the suspension of "AQUATERIC" in glycerol. Squalane can be used instead of glycerol.

The method of the present invention can be used to prevent the transmission of human immunodeficiency virus, such as HIV-1 and HIV-2, and herpesvirus, in humans. The present invention is thus effective for preventing the transmission of HIV-1, or HSV, such as HSV-1, HSV-2, HSV-7 and HSV-8, as well as human cytomegalovirus, varicella-zoster virus, Epstein-Barr virus and human herpesvirus 6. Preferred embodiments of the present invention are for preventing the transmission of HIV-1, HSV-1, or HSV-2, which are known to be transmitted sexually and HSV-8, which is known to be a causative agent of Kaposi's sarcoma.

The present invention also concerns preventing the transmission of or treating a sexually transmitted bacterial infection such as syphillis, gonorrhea, chlamydia, *trichomoniasis* or an infection caused by *garderella vaginalis*.

In the methods of the present invention for preventing the transmission of HIV or herpesvirus infection in a human or for preventing the transmission of or for treating a sexually transmitted bacterial infection in a human, a pharmaceutically effective anti-viral amount or anti-bacterial amount, respectively, of CAP or HPMPC or both CAP and HPMPC is administered to a human. The composition for use in the present invention is administered to an appropriate region of the human body.

The phrase "administration to an appropriate region of the body" includes, for example, application of the (active ingredient (CAP or HPMPC or both) or a composition containing the same used to regions of the body of a human, for example, the region of the human body which comes into close contact with another human body, for example, application (directly or indirectly) to the male or female genitalia to prevent transmission of HIV-1, HSV-1, HSV-2 or bacterial infection during sexual intercourse.

The term "local administration" includes any method of administration in which the activity of the CAP or HPMCP or both used in the present invention is substantially confined to the region of the human's body to which it is applied, i.e., vaginal or rectal (topical) administration.

The present invention is thus particularly effective for providing a method of preventing the transmission of a viral infection such as HIV or herpesvirus infection or preventing the transmission of or treating a bacterial infection which is transmitted by sexual contact, such as vaginal transmission, either during sexual intercourse or during childbirth (vaginal delivery), by vaginal administration, such as by administering a cream, ointment, lotion, jelly, solution, emulsion or foam formulation containing a pharmaceutically effective anti-HIV-1 amount or anti-HSV amount or anti-bacterial amount of CAD (such as micronized CAP) or HPMCP (such as micronized HPMCP) or both, either alone or in combination with a pharmaceutically acceptable carrier or diluent.

To prevent transmission of HIV-1 or herpesvirus infection or a bacterial infection which is transmitted by sexual contact, CAP or HPMCP (in micronized form) or both can be applied to a contraceptive device (for example, a male or female condom, a contraceptive diaphragm or a contraceptive sponge, for example, a polyurethane foam sponge), prior to sexual intercourse.

Alternatively, CAP or HPMCP or both can be applied on a pessary or tampon for vaginal administration. The pharmaceutical formulation for topical administration would comprise a pharmaceutically effective anti-HIV amount or anti-herpesvirus amount or anti-bacterial amount of CAP or HPMCP or both and at least one pharmaceutically acceptable topical carrier or diluent, to form an ointment, cream, gel, lotion, paste, jelly, spray or foam.

The amount (dosage) of the active ingredient (CAP or HPMCP or both) in a topical formulation for use in the present invention will, in general, be less than 1,000 milligrams, preferably between 200 to 800 milligrams.

It is preferable to administer the active ingredient in conjunction with a pharmaceutically acceptable diluent or carrier, as a pharmaceutical formulation. The present invention thus also involves the use of a pharmaceutical formulation or composition comprising the active ingredient together with one or more pharmaceutically acceptable carriers or diluents and, optionally, other prophylactic ingredients. The carrier(s) or diluent(s) should be "acceptable" in the sense of being compatible with the other ingredients of the formulation and not deleterious to the recipient.

Pharmaceutical formulations include those suitable for vaginal, rectal or topical administration. The formulations may, where appropriate, be conveniently presented in discrete dosage units and may be prepared by any of the methods well known in the art of pharmacy. All such methods include the step of bringing into association the active ingredient with liquid carriers, gels or finely divided solid carriers or both and then, if necessary, shaping the product into the desired formulation.

Formulations suitable for vaginal administration may be presented as pessaries, tampons, creams, gels, pastes, jelly, foams or sprays or aqueous or oily suspensions, solutions or emulsions (liquid formulations) containing in addition to the active ingredient, such carriers as are known in the art to be appropriate. These formulations are useful to protect not only against sexual transmission of HIV or HSV or a sexually transmitted bacterial infection, but also to prevent infection of a baby during passage through the birth canal. Thus the vaginal administration can take place prior to sexual intercourse, during sexual intercourse, and immediately prior to childbirth.

As a vaginal formulation, the active ingredient may be used in conjunction with a spermicide and as discussed above, may be employed with a condom, a diaphragm, a sponge or other contraceptive device.

Pharmaceutical formulations and preparations suitable for administration may conveniently be presented as a solution, an aqueous or oily suspension, or an emulsion. The active ingredient may also be presented as a bolus, electuary or paste.

Liquid preparations for vaginal administration may contain conventional additives such as suspending agents, emulsifying agents, non-aqueous vehicles (which may include edible oils) or preservatives.

Pharmaceutical formulations suitable for rectal administration, wherein the carrier is a solid, are most preferably represented as unit dose suppositories. Suitable carriers include cocoa butter and other materials commonly used in the art, and the suppositories may be conveniently formed by admixture of the active compound with the softened or melted carrier(s) followed by chilling and shaping in molds.

Drops may be formulated with an aqueous or non-aqueous base comprising one or more dispersing agents, solubilizing agents or suspending agents. Liquid sprays are conveniently delivered from pressurized packs.

When desired, the above described formulations adapted to give sustained release of the active ingredient may be employed.

The pharmaceutical compositions for use according to the invention may also contain other active ingredients such as spermicides, or antimicrobial agents, preservatives or other anti-viral agents.

The micronized CAP and its suspension in glycerol or squalane according to the present invention results in an active and stable formulation which has antiviral activity and is suitable for topical application to prevent the sexual transmission of HIV-1, herpesviruses and sexually transmitted bacterial infections.

The present invention also relates to pharmaceutical compositions containing 1 to 25 wt. %, preferably 5 to 20 wt. % and, more preferably, 12 to 18 wt. % of micronized cellulose acetate phthalate and glycerol and either polyvinylpyrrolidone and Crospovidone (1-ethenyl-2-pyrrolidinone homopolymer), or colloidal silicon dioxide, to form an easily applicable homogeneous cream.

In addition to the two formulations disclosed above, a semi-solid formulation containing all solid ingredients (i.e., "AQUATERIC", povidone, Crospovidone and colloidal silicone dioxide) can be mixed with glycerol or squalane wherein the amounts of all the comoponents are sufficient to result in a semi-solid dough or putty which can be easily shaped, aliquotted into desired portions and packaged for protection from environmental factors (humidity, etc.).

Moreover, the "AQUATERIC" can be replaced by another form of micronized CAP. This could be obtained, for example, by dissolving 100 mg of CAP and 100 mg of polyvinylpyrrolidone (povidone, PVP) per 1 ml of dimethyl sulfoxide. After dissolution of the solid components, water is slowly added under efficient, vigorous mixing. This will result in the formation of a fine precipitate of CAP containing PVP. The precipitate is subsequently washed with water and finally freeze-dried. The fine, freeze-dried powder can be used instead of "AQUATERIC".

The procedure disclosed in the preceding paragraph is much simpler than a similar procedure utilizing polyvinyl alcohol instead of PVP, and acetone instead of dimethyl sulfoxide, and also requires the presence of a mineral salt, such as magnesium chloride (U.S. Pat. No. 4,968,350 to Bindschaedler et al., "Process for Preparing a Powder of Water-insoluble Polymer which can be Redispersed in a Liquid Phase, the Resulting Powder and Utilization Thereof"). The presence of $Mg^{++}$ is also undesirable, since it decreases the stability of CAP.

The aforementioned formulation of "AQUATERIC", PVP and Crospovidone in glycerol is suitable for topical application. However, in order to apply (administer) the formulation in predetermined quantities, in addition to the formulation, a measuring device, e.g., an applicator, should be provided.

It will be advantageous to incorporate the formulations containing CAP and/or HPMCP into hydroxypropyl methylcellulose capsules such as "VEGI CAPS" or "VEGGIE-CAPS", manufactured by GS Technologies, Springville, Utah, which can be configured as vaginal suppositories. This would reduce costs and avoid possible disposal problems. Such suppositories can be inserted into the vagina intact, whereby the shell of the capsule will soften and rupture upon interaction with moisture within the vagina, thus releasing the CAP and/or HPMCP formulation.

For example, the above-described hydroxypropyl methylcellulose capsules can be filled either with:

(a) "AQUATERIC" suspended in glycerol; or (b) "AQUATERIC" in solid form, with or without additional inactive ingredients, can also be incorporated in gelatin capsules.

The formulation containing the active ingredient (CAD and/or HPMCP) of the present invention can be in the form of a single capsule or the formulation may be in the form of two or more capsules, each containing the same or distinct ingredients.

Applicants discovered that two of many pharmaceutical excipients display a potent anti-HIV-1 activity effect and anti-bacterial effect. This is of enormous importance since excipients are inexpensive compounds. The expected dose of CAP or HPMCP per single topical application (approximately 300 mg) is expected to cost approximately 1.33 US cents. Thus, the application of CAP and/or HPMCP for decreasing the frequency of sexual transmission of HIV-1 and bacterial infections is economically feasible worldwide and is expected to contribute to the control of the worldwide HIV-1 epidemic.

Since viruses other than HIV-1 are also transmitted sexually, it was of interest to determine whether CAD and/or HPMCP may also inhibit infection by such viruses. Herpesvirus type 1 (HSV-1) and type 2 (HSV-2) were selected for these experiments. Results summarized in FIG. 1 indicate that CAP inhibited infection by both HSV-1 and HSV-2. Similar results were obtained with HPMCP (see FIG. 2).

Some of the results presented herein were briefly summarized under the code "microbicide B195" at the 12th World AIDS Conference, Neurath, A. R., Strick, N., Lin, K. et al., "Microbicide B195", *Proceedings of the 12th World AIDS Conference,* Geneva, Switzerland, Jun. 28–Jul. 3, 1998, pp. 239–242.

EXAMPLES

Example 1:
Screening Pharmaceutical Excipients for Anti-HIV Activity

All compounds were first screened for anti-HIV-1 activity by measuring the inhibition of fusion between HIV-1 infected and uninfected cells (Jiang, S., Lin, K., Strick, N., Neurath, A. R., "Inhibition of HIV-1 Infection by a Fusion Domain Binding Peptide from the HIV-1 Envelope Glycoprotein gp41", *Biochem. Biophys. Res. Commun.* (1993), 195, 533–538).

The selection of pharmaceutical excipients to screen for anti-HIV activity was made from a list of pharmaceutical excipients derived from the *Handbook of Pharmaceutical Excipients,* edited by Ainley Wade and Paul J. Weller, $2^{nd}$ edition, American Pharmaceutical Association, Washington, D.C., and the Pharmaceutical Press, London, (1994). The selected compounds are listed in the following Table 1A. Other excipients listed in the *Handbook of Pharmaceutical Excipients* were not tested for anti-HIV-1 activity, since it was known from earlier studies that they do not have such activity (see the following Table 2). Compounds insoluble in water or buffers (see the following Table 3), organic compounds including oils, waxes, solvents and detergents known to solubilize cell membranes and envelopes of lipid-containing viruses (see the following Table 4), gases used for aerosol propellants (see the following Table 5), and oxidizing agents and disinfectants with antibacterial activity (see the following Table 6) were excluded from the screening process.

Surprisingly, of all the compounds listed in Table 1A, only two compounds inhibited fusion between HIV-1 infected and uninfected cells, corresponding to a method for rapidly assessing the anti-HIV-1 activity of compounds. In this assay, HIV-1 IIIB infected H9 cells were labeled by 2',7'-bis-(2-carboxyethyl)-5-(and-6)-carboxyfluorescein acetoxymethyl ester (BCECF; Molecular Probes, Inc., Eugene, Oreg.) according to the manufacturer's instructions. BCECF-labeled H9/HIV-1 IIIB cells ($10^4$) were mixed with $2 \times 10^5$ uninfected MT-2 cells. After incubation in a 96-well plate at 37° C. for 1 hour, the fused and unfused labeled cells were counted under an inverted fluorescence microscope at a 160×magnification. At least 200 BCECF-labeled cells were counted and the proportion of fused cells was determined. These tests were carried out in the presence and absence of graded quantities of compounds to be screened. All experiments with HIV-1 were carried out under P2 biohazard containment levels.

The anti-HIV-1 activity of the two compounds, namely cellulose acetate phthalate and hydroxypropyl methylcellulose phthalate, listed in Table 1A was confirmed and quantitated by the following additional tests: (a) inhibition of the cytopathic effect (CPE) of HIV-1 and (b) inhibition of production of the HIV-1 nucleocapsid antigen (p24) (Neurath, A. R., Strick, N., Haberfield, P., Jiang, S., "Rapid Prescreening for Antiviral Agents Against HIV-1 Based on their Inhibitory Activity in Site-Directed Immunoassays, II. Porphyrins Reacting with the V3 loop of gp120", *Antivir. Chem. Chemother.*, (1992), 3, 55–63) (Table 1B). The two compounds were not toxic for uninfected cells at concentrations $\leq 2,500$ μg/ml.

$10^4$ MT-2 cells in 96-well plates were infected with HIV-1 (a dose sufficient to accomplish a multiplicity of injection of 0.0045) in 200 μl of RPMI 1640 medium supplemented with 10 vol. % fetal bovine serum ("FBS"). After 1 hour and 24 hours, half of the culture medium was changed and replaced by fresh medium. On the fourth day after incubation at 37° C., 100 μl of culture supernatants were collected from each well and an equal volume of fresh medium was added to the wells. The collected supernatants were mixed with an equal volume of 5 vol. % TRITON X-100 and assayed for the p24 antigen using an ELISA (Enzyme-linked immunoassay) kit from Coulter Immunology (Hialeah, Fla.). On the sixth day after infection, an indicator, XTT Tetrazolium Dye (1 mg/ml; 50 μl/well; PolySciences, Inc., Warrington, Pa.) was added to the cells. After 4 hours, intracellular formazan was determined colorometrically at 450 nm following the described procedure (Weislow O. S., Kiser, R., Fine, D. L. et al., "New Soluble-Formazan Assay for HIV-1 Cytopathic Effects: Application to High-Flux Screening of Synthetic and Natural Products for AIDS-Antiviral Activity", *J. Natl. Cancer Inst.*, 81, 577–586, (1989)). The percentage of cytopathogenesis was calculated using the following formula: $100 \times [(OD_{450}$ in negative control$-OD_{450}$ in experiment)/$(OD_{450}$ in negative control$-OD_{450}$ in positive control)]. The negative control corresponded to cells mixed with culture medium, instead of HIV-1, while the positive control represented cells mixed with 100 $CCID_{50}$ (tissue culture infectious doses) of HIV-1 IIIB, which lysed 100% of the MT-2 cells. The cytopathic effect ("CPE") of the compounds on uninfected cells was measured using the same methodology.

Pharmaceutical excipients, except compounds insoluble in water, detergents and oxidizing agents, were screened for anti-HIV-1 activity by an assay measuring fusion between infected and uninfected cells. Only two compounds, cellulose acetate phthalate (CAP) and hydroxypropyl methylcellulose phthalate (HPMCP), had inhibitory activity. Another polymeric phthalate, vinyl acetate phthalate, had no inhibitory activity. Other cellulose derivatives, for example, carboxymethylcellulose, also lacked activity. The two selected compounds, CAP and HPMCP, also inhibited HIV-1 infection, as measured by inhibition of the cpe and of the production of the HIV-1 nucleocapsid antigen p24 (Table 1B). The two compounds were not toxic for uninfected cells at concentrations $\geq 2,500$ μg/ml. The anti-HIV-1 activity of CAP was better than that of HPMCP, but both compounds provided desirable results.

Since herpesviruses are also frequently transmitted sexually, it was of interest to determine whether CAP might also inhibit infection by these viruses. Herpesvirus type 1 (HSV-1) and type 2 (HSV-2) were selected to test this possibility. Results summarized in FIG. 1 indicate that CAD inhibited infection by both HSV-1 and HSV-2. Similarly, CAD inhibited infection by HCMV. With respect of FIG. 1, virus preparations were tested for infectivity using a readout system based on the quantitation of β-galactosidase (absorbance at 410 nm).

TABLE 1A

Pharmaceutical Excipients Tested for Anti-HIV-1 Activity

| COMPOUND | Inhibition of Cell Fusion *$ED_{50}$ ± SD (μg/ml) |
|---|---|
| Acacia | —** |
| Acesulfame Potassium | — |
| Alginic Acid | — |
| Ascorbyl Palmitate | — |
| Aspartame | — |
| Benzyl Benzoate | — |
| Bronopol | — |
| Butylated Hydroxyanisole | — |
| Butylated Hydroxytoluene | — |
| Butylparaben | — |
| Carbomer 934P | — |
| Carboxymethylcellulose | — |
| Cellulose Acetate Phthalate | 51.91 ± 1.32 |
| Chlorocresol | — |
| Croscarmellose Sodium | — |
| Dextrates | — |
| Dibutyl Sebacate | — |
| Ethylparaben | — |
| Hydroxyethyl Cellulose | — |
| Hydroxypropyl Cellulose | — |
| Hydroxypropyl Methylcellulose | — |
| Hydroxypropyl Methylcellulose Phthalate | 68.30 ± 11.48 |
| Imidurea | — |
| Maltodextrin | — |
| Maltol | — |
| Menthol | — |
| Methylcellulose | — |
| Methylparaben | — |
| Poloxamer | — |
| Polymethacrylates | — |
| Povidone | — |
| Propyl Gallate | — |
| Propylene Carbonate | — |
| Propylene Glycol Alginate | — |
| Propylparaben | — |

TABLE 1A-continued

Pharmaceutical Excipients Tested for Anti-HIV-1 Activity

| COMPOUND | Inhibition of Cell Fusion *$ED_{50}$ ± SD ($\mu$g/ml) |
|---|---|
| Saccharin | — |
| Sodium Alginate | — |
| Sodium Cyclamate | — |
| Sodium Starch Glycolate | — |
| Sodium Stearyl Fumarate | — |
| Sorbic Acid | — |
| Pregelatinized Starch | — |
| Triacetin | — |
| Vanillin | — |
| Vinylacetate Phthalate | — |
| Xanthan Gum | — |

*$ED_{50}$ = Effective dose for 50% inhibition of HIV-1 induced cell fusion.
**— = means no inhibitory activity on HIV-1 induced cell fusion at the final concentration of 1000 $\mu$g/ml.

TABLE 1B

Pharmaceutical Excipients Tested for Anti-HIV-1 Activity

| Inhibition of HIV-1 Infection | Cellulose Acetate Phthalate | | Hydroxypropyl Methylcellulose Phthalate | |
|---|---|---|---|---|
| | $ED_{50}$* ± SD ($\mu$g/ml) | $ED_{90}$* ± SD ($\mu$g/ml) | $ED_{50}$* ± SD ($\mu$g/ml) | $ED_{90}$* ± SD ($\mu$g/ml) |
| P24 Production | 2.54 ± 0.16 | 4.76 ± 1.05 | 4.76 ± 1.20 | 8.86 ± 1.11 |
| CPE | 3.68 ± 0.74 | 7.62 ± 1.66 | 7.79 ± 1.30 | 15.62 ± 7.61 |
| Cell Fusion | 51.91 ± 1.32 | 94.89 ± 3.12 | 68.30 ± 11.48 | 157.32 ± 32.86 |

*$ED_{50(90)}$ = Effective dose(s) for 50% (90%) inhibition of HIV-1 mediated p24 production, CPE and cell fusion.

TABLE 2

Compounds Known Not to Have Anti-HIV-1 Activity

Albumin
Alpha Tocopherol
Ascorbic Acid
Benzoic Acid
Benzyl Alcohol
Dibasic Calcium Phosphate
Calcium Sulfate
Cholesterol
Citric Acid Monohydrate
Cyclodextrins
Dextrin
Dextrose
Diethanolamine
Diethyl Phthalate
Edetic Acid
Ethyl Maltol
Ethyl Vanillin
Fructose
Fumaric Acid
Gelatin
Liquid Glucose
Glycerin
Guar Gum
Lactic Acid
Lactose
Malic Acid
Maltitol Solution
Mannitol
Meglumine
Monoethanolamine
Polyethylene Glycol
Polyvinyl Alcohol
Potassium Chloride
Potassium Citrate
Potassium Sorbate
Propylene Glycol
Sodium Bicarbonate
Sodium Chloride
Sodium Citrate Dihydrate
Sodium Metabisulfite
Dibasic Sodium
Monobasic Sodium
Sodium Propionate
Sorbitol
Starch
Sterilizable Maize Starch
Sucrose
Compressible Sugar
Confectioner's Sugar
Sugar Spheres
Tartaric Acid
Thimerosal
Triethanolamine
Triethyl Citrate
Xylitol

TABLE 3

Compounds Insoluble in Water or Buffers

Bentonite
Calcium Carbonate
Calcium Stearate
Carboxymethylcellulose Calcium
Microcrystalline Cellulose
Powdered Cellulose
Cetostearyl Alcohol
Cetyl Alcohol
Cetyl Esters Wax
Crospovidone
Ethylcellulose
Kaolin
Magnesium Aluminum Silicate
Magnesium Carbonate
Magnesium Oxide
Magnesium Stearate
Magnesium Trisilicate
Polacrilin Potassium
Shellac
Colloidal Silicon Dioxide
Suppository Bases
Talc
Titanium Dioxide
Tragacanth
Zein
Zinc Stearate

TABLE 4

Organic Compounds, Oils, Waxes and Solvents and Detergents Solubilizing Cell Membranes and Envelopes of Lipid Containing Viruses Alcohol
Benzalkonium Chloride
Benzethonium Chloride
Canola Oil
Hydrogenated Castor Oil
Cetrimide
Corn Oil
Cottonseed Oil
Docusate Sodium

TABLE 4-continued

Organic Compounds, Oils, Waxes and Solvents and Detergents
Solubilizing Cell Membranes and Envelopes of Lipid Containing Viruses Ethyl Oleate
Glyceryl Monooleate
Glyceryl Monostearate
Glyceryl Palmitostearate
Glycofurol
Isopropyl Alcohol
Isopropyl Myristate
Isopropyl Palmitate
Lanolin
Lanolin Alcohols
Hydrous Lanolin
Lecithin
Medium Chain Triglycerides
Mineral Oil
Light Mineral Oil
Mineral Oil and Lanolin Alcohols
Oleic Acid
Paraffin
Peanut Oil
Petrolatum
Petrolatum and Lanolin Alcohols
Polyoxyethylene Alkyl Ethers
Polyoxyethylene Castor Oil Derivatives
Polyoxyethylene Sorbitan Fatty Acid Esters
Polyoxyethylene Stearates
Sesame Oil
Sodium Lauryl Sulfate
Sorbitan Esters (Sorbitan Fatty Acid Esters)
Soybean Oil
Stearic Acid
Stearyl Alcohol
Hydrogenated Vegetable Oil Type 1
Anionic Emulsifying Wax
Carnauba Wax
Microcrystalline Wax
Nonionic Emulsifying Wax
White Wax
Yellow Wax

TABLE 5

Gases Used for Example in Aerosol Propellants

Butane
Carbon Dioxide
Chlorodifluoroethane
Chlorodifluoromethane
Dichlorodifluoromethane
Dichlorotetrafluoroethane
Difluoroethane
Dimethyl Ether
Isobutane
Nitrogen
Nitrous Oxide
Propane
Tetrafluoroethane
Trichloromonofluoromethane

TABLE 6

Oxidizing Agents and Disinfectants

| | | |
|---|---|---|
| Chlorhexidine | Phenol | Phenylmercuric Acetate |
| Chlorobutanol | Phenoxyethanol | Phenylmercuric Borate |
| Cresol | Phenylethyl Alcohol | Phenylmercuric Nitrate |

Example 2:
Formulations of CAP

The formulation of CAP and HPMCP for topical vaginal application as an antiviral agent or virucide to prevent the sexual transmission of HIV-1 and herpesviruses, respectively, represented a difficult challenge which could be overcome only by innovative approaches. Both CAP and HPMCP are insoluble in water and can be solubilized in water by adjusting the pH of the environment to ≈6 or above (*Handbook of Pharmaceutical Excipients*, 2nd Edition, edited by Ainley Wade and Paul J. Weller, American Pharmaceutical Association, Washington, (1994)), or by the use of appropriate organic solvents. On the other hand, vaginal secretions from healthy, reproductive-age women are characteristically acidic (pH values of 3.4 to 6.0) (S. Voeller, D. J. Anderson, "Heterosexual Transmission of HIV", *JAMA*, 267, 1917–1918, (1992)). Consequently, the topical application of a formulation in which either CAP or HPMCP would be soluble (i.e., pH=$\geq$6) would be expected to contribute to a vaginal environment which is physiologically undesirable. Nevertheless, attempts were made to formulate CAP or HPMCP in gels/creams which are customarily used for vaginal applications as moisturizers and/or contraceptive agents. These included the following: hydroxyethylcellulose gels (e.g., K-Y JELLY, Johnson and Johnson, Raritan, N.J.); carbomer 934P based gels (e.g., REPLENS, Roberts Pharmaceuticals, Inc., Mississauga, Ontario, Canada; Taro gel, Taro Pharmaceuticals, Inc., Bramalea, Ontario, Canada); hydroxypropyl methylcellulose and carbomer 934P based gels (e.g., H-R lubricating jelly, Carter-Wallace, Inc., New York, N.Y.); polyglyceryl methacrylate (Gyne-Moistrin Moisturizing Gel (Shering-Plough Healthcare Products, Inc., Mississauga, Ontario, Canada)), and gels containing carbomer 934P and hydroxypropyl methylcellulose alone. All the aforementioned formulations have water as their major constituent. When the preparations of CAP and HPMCP in the above gels were submitted to accelerated stability studies for 7 days at 45° C. and subsequently tested for anti-HIV-1 activity, no antiviral activity was detected. This was probably due to the hydrolysis of each of these cellulose derivatives, resulting in the release of acetic and phthalic acids and leading to diminished anti-HIV-1 activity.

To avoid this problem, it was decided to dissolve the cellulose derivatives (experiments were carried out mostly with CAP which has higher anti-HIV-1 activity in comparison with HPMCP; see Table 1B herein) in organic solvents that are low in water content, yet water miscible for in vivo compatibility, and nontoxic to vaginal mucosa, selected on the basis of preliminary studies. These solvents included the following: propylene glycol, propylene carbonate, benzyl alcohol, polyethylene glycol (PEG 400), dimethyl isosorbide, and ethoxydiglycol ("TRANSCUTOL"). The solubility of CAP in these solvents ranges between 5.3 to 30% (w/w). To increase the viscosity of these solutions, it was necessary to use them as gels/creams for topical applications. Either polyvinyl pyrrolidone (PVP) and/or different poloxamers (e.g., Pluronic F68) were added to the CAD solutions in the different organic solvents. To estimate the properties of the different formulations after contact with a physiological environment, they were mixed with water or physiological saline (0.14 M NaCl). Under these conditions, CAP precipitated at the interface of the formulations with water (saline) in the form of a large polymeric mass which would not be expected to have antiviral activity and would not be appropriate for topical application. It was possible to overcome this problem by incorporating into the CAP containing formulation compounds which increase the pH upon contact with water or a saline solution (=0.14 M NaCl), e.g., sodium acetate or triethanolamine. Inclusion of the latter compounds into the formulation eliminated or diminished the problem of appearance of large CAP aggregates.

Surprisingly, accelerated stability studies (incubation for 7 days at 45° C.) of CAP in the above organic pharmaceutical excipients/solvents, containing in addition the aforementioned gelling and buffering agents, resulted in complete loss of anti-HIV-1 activity. This activity was retained if the buffering agents were omitted and added only before initiating the assay for anti-HIV-1 activity. Thus, in summary, the CAP formulations in organic solvents containing also a buffering agent represent formulations unsuitable for topical applications, either because the active ingredient, CAP, precipitates from the formulation in a large polymeric mass upon contact with physiological fluids (in the absence of appropriate buffering agents incorporated into the formulation) or are converted into useless formulations lacking anti-HIV-1 activity, because of inactivation of the active ingredient, CAP.

To avoid the above problems, the possibility of using CAP in the form of a micronized preparation in suspension was explored. This necessitated the use of a solvent in which CAP would not be soluble, since otherwise the results obtained would be expected to be exactly the same as were those referred to above. A solvent with such properties is actually water in which neither CAP nor HPMCP are soluble (*Handbook of Pharmaceutical Excipients*, 2nd Edition, edited by Ainley Wade and Paul J. Weller, American Pharmaceutical Association, Washington (1994)).

A formulation containing water and a commercially available micronized form of CAP ("AQUATERIC" from the FMC Corporation, Philadelphia, Pa.), containing in addition to CAP (63 to 70 wt %), poloxamer and distilled acetylated monoglycerides, was prepared. Thickening agents, i.e., PVP and/or pluronic F68, were added to the water suspension of the "AQUATERIC". When this gel was submitted to accelerated stability studies (7 days at 45° C.) and then tested for anti-HIV-1 activity, essentially no antiviral activity was recovered. Thus, another solvent was needed in which the CAP ("AQUATERIC") would not be soluble and would not lose antiviral activity. Surprisingly, glycerol (very similar to propylene glycol in which CAP is soluble to ≈30% w/w) meets both these requirements. Based on this discovery, a formulation of CAP ("AQUATERIC") was prepared as follows: 200 mg of PVP (MW 40,000, Spectrum) were dissolved in 1 ml of glycerol. Subsequently, 50 mg of Crospovidone (Polyplasdone INF-10, ISP Technologies) were suspended in the solution followed by the addition of 286 mg of "AQUATERIC". The PVP and Crospovidone were added to prevent the separation of the "AQUATERIC" microsuspension from glycerol. The resulting formulation maintained its uniformity over time and also its anti-HIV-1 activity following an accelerated stability test carried out under conditions described above.

In summary, the following properties of CAD dictated its formulation: (a) low solubility in aqueous solutions at pH<6, (b) hydrolysis during storage in aqueous solutions at room temperature, and (c) solubility in several biocompatible organic solvents; for example, propylene carbonate, propylene glycol and polyethylene glycol, from which CAP precipitates upon contact with aqueous solvents. To avoid these problems, a formulation of micronized CAP in glycerol (in which CAP is not soluble), "CAP Formulation I", was prepared.

"CAP Formulation I" is a preparation of micronized CAP ("AQUATERIC" containing 66–73% of CAP, a polyoxyethylene-polyoxypropylene block copolymer and distilled acetylated monoglycerides, used in aqueous media as an enteric film-coating liquid (FMC Corporation, Philadelphia, Pa.)), (15.9 g) was mixed with glycerol (70.2 g) and polyvinylpyrrolidone K-30 (Spectrum Quality Products, Inc., New Brunswick, N.J.) (11.1 g) and Crospovidone NF (ISP Technologies, Inc., Wayne, N.J.) (2.8 g) were added in order to maintain the micronized CAP in suspension.

Another formulation, "CAP Formulation II", was prepared by replacing polyvinylpyrrolidone+Crospovidone with colloidal silicon dioxide M-5P (Cabot Corp., Cab-O-Sil Division, Tuscola, Ill.), an excipient with an established use in vaginal preparations. CAP Formulation II contained 23.7 g "AQUATERIC" and 7.89 g silica per 100 g glycerol.

All components of these two CAP Formulations were USP grade and have been approved for human medicinal use.

Example 3

Measurement of Inhibitory Ability Against HSV-1 and HSV-2 and Against HCMV

The following method was used to measure the inhibitory activity: 500 µl of compounds (at distinct dosages) in Eagle's Minimum Essential Medium (EMEM) were mixed with an equal volume of appropriately diluted infectious HSV-1 or HSV-2. The mixture was added to ELVIS HSV cells in 24-well plates. The ELVIS cells as well as the media were provided by Diagnostic Hybrids, Inc. (Athens, Ohio).

ELVIS cells are derived by selection of G400-resistant colonies following cotransfection of baby hamster kidney cells with a plasmid which contains a G418-antibiotic-resistant marker and a plasmid which contains an *Escherichia coli* LacZ gene placed behind an inducible HSV promoter. The promoter is from HSV-1 UL39 which encodes ICP6, the large subunit of ribonucleotide reductase (RR1). This promoter has a number of features which make it ideal for the detection of HSV. First, there is no constitutive expression from this promoter in uninfected cells. Second, activation of the promoter appears to be specific for HSV. Third, expression from this promoter occurs within hours after infection. Fourth, this promoter is strongly transactivated by the virion associated trans-activator protein VP16. As early as six hours after infection, HSV-infected cells can be detected by histochemical staining for β-galactosidase activity (Stabell E. C. and Olivo P. D., "Isolation of a Cell Line for Rapid and Sensitive Histochemical Assay for the Detection of Herpes Simplex Virus", *J. Virological Methods*, 38, 195–204, (1992)).

Twenty four hours after HSV infection, in the presence and absence of graded quantities of the test compounds, the ELVIS cells were lysed with TRITON X-100 and β-galactosidase in the cell lysates was determined by an ELISA kit provided by Five Prime→Three Prime, Inc. (Boulder, Colo.). This ELISA kit is capable of detecting and quantitating picogram levels of *E. coli* β-galactosidase protein expressed in transformed bacteria or eukaryotic cells and tissues. The method is based on detection of the β-galactosidase protein rather than on the enzymatic activity. β-galactosidase from *E. coli* is a tetrameric enzyme composed of four identical subunits. The individual subunits do not exhibit enzyme activity and therefore are not detectable by standard enzyme activity assays. The Five Prime→Three Prime β-galactosidase ELISA kit overcomes this limitation by detecting the actual protein that is expressed.

The surprising conclusion of the described experiments was that cellulose acetate phthalate and hydroxypropyl methylcellulose phthalate, of all the excipients tested, were unique in having potent antiviral activity against both HIV-1 and HSV-1 and HSV-2, and against other viruses belonging to the herpesvirus group. Alternately, antiviral activity against HSV-1 was measured using HSV vgCL5, a recombinant virus in which the expression of β-galactosidase ("β-gal") is under the control of the HSV-1 late gene gC regulatory region (Weir, J. P., Steffy, K. R., Sethna, M., "An Insertion Vector for the Analysis of Gene Expression During Herpes Simplex Virus Infection", *Gene* 91990), 89, 271–274).

In this test, 50 μl of MEM tissue culture medium containing 5% FBS and graded concentrations of CAP was mixed with 100 μl of Vero cells in the same FBS-containing medium ($10^6$ cells/ml) for 30 minutes at 25° C. Subsequently, 50 μl of HSV vgCL5, at a dilution sufficient to infect approximately 50% of cells, as determined by in situ staining for β-galactosidase, was added and the mixture was placed into wells of 96-well plates. After incubation at 37° C. for 24 hours, the cells were either immediately lysed or frozen for 1 to 5 days for storage and subsequently lysed by adding to the cells and medium, 50 μl of 2.5% (v/v) TRITON X-100, containing protease inhibitors (PMSF, leupeptin and pepstatin, all at 10 μg/ml). β-galactosidase in the lysed preparations was detected by the ELISA kit from Five Prime→Three Prime.

Inhibitory activity against human cytomegalovirus (HCMV) was measured using the HCMV strain RC-256 (ATCC VR-2536), a recombinant of HSMV Towne containing the *E.coli* LacZ gene (Spaete, R. R., Mocarski, E. S., "Regulation of Cytomegalovirus Gene Expression: α and β Promoters Are Trans Activated by Viral Functions in Permissive Human Fibroblasts", *J. Virol.*, (1985), 56, 135–143).

The inhibitory effect on CMV on replication of the β-galactosidase expressing HCMV RC-256 was measured under conditions similar to those described for HSV vgCL5, except that the cell-virus mixtures were kept for 48 hours at 37° C. before measuring β-galactosidase levels and human foreskin fibroblast (HFF) cells were used.

Example 4
Virucidal Activity of CAP Formulations

Figure 2:
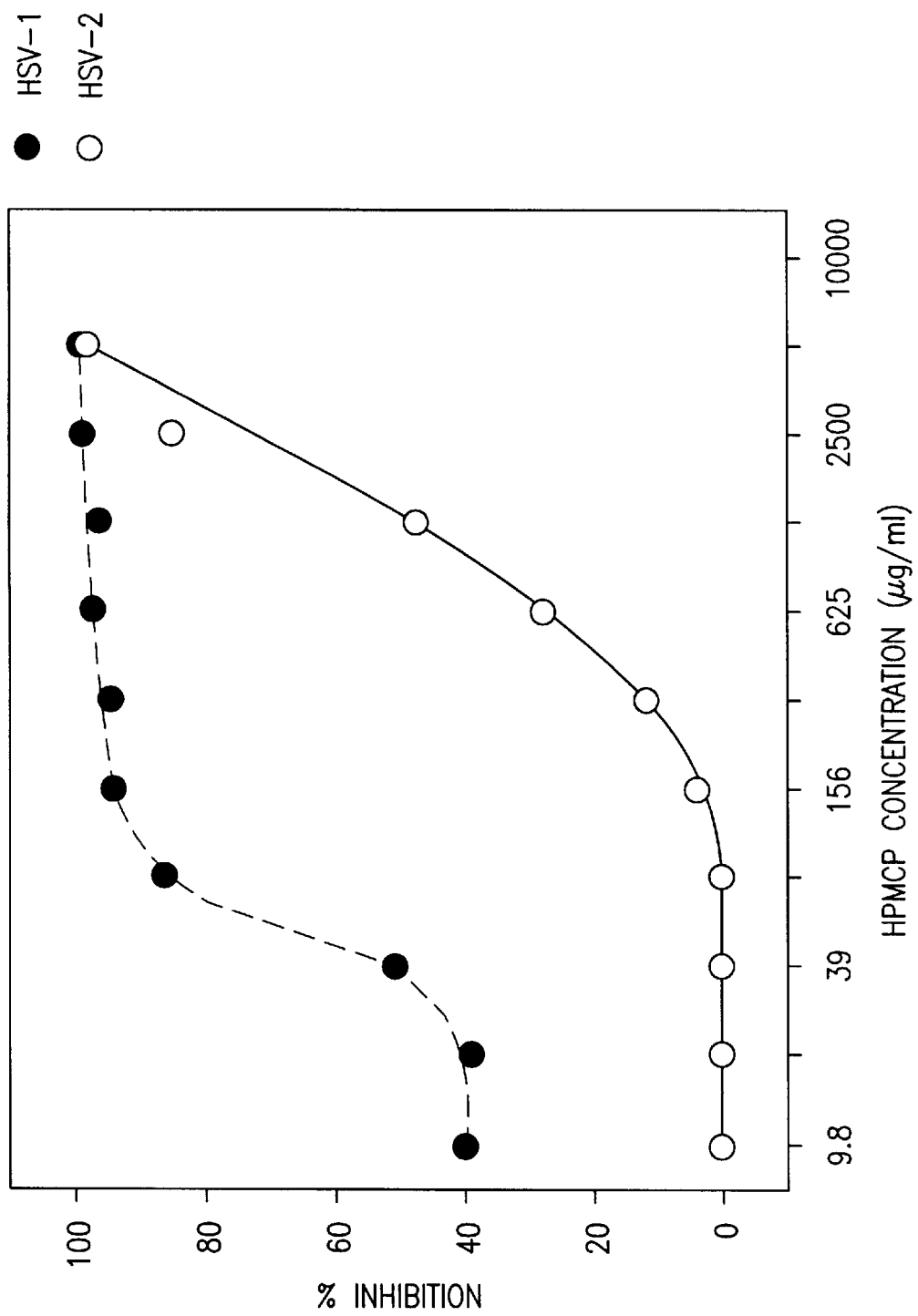
FIG. 2 is a graph of % inhibition vs. HPMCP concentration, for HSV-1 and HSV-2. The results shown in FIG. 2 are similar to those shown in FIG. 1.

Both the anti-HIV-1 activity and the anti-HSV-1 and anti-HSV-2 activities of the CAP formulation, before or after stability testing, corresponded to the content of CAP in the preparation and to results shown in Table 1B and FIGS. 1 and 2 for HIV-1 and herpesviruses, respectively.

Figure 3:
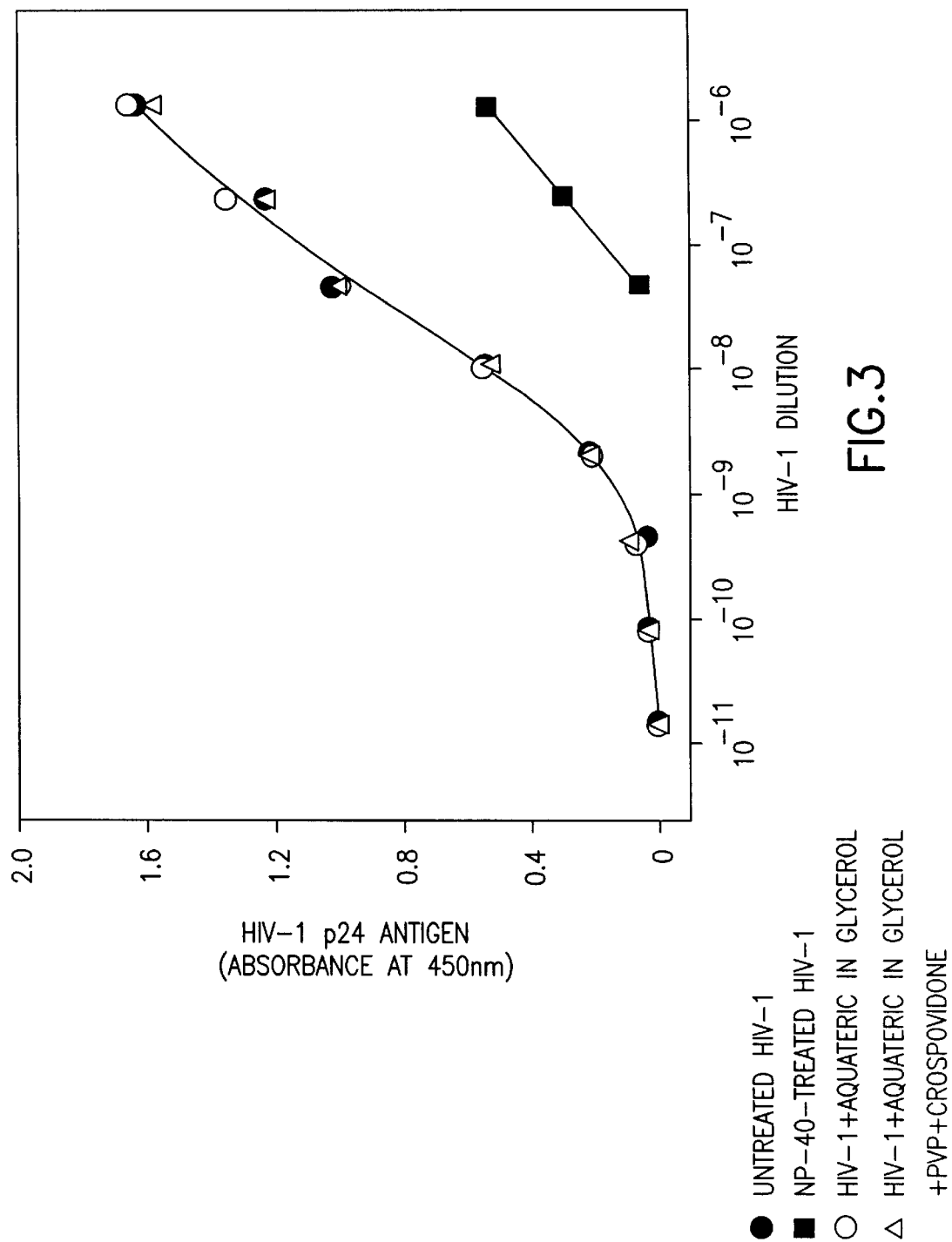
FIG. 3 is a graph of HIV-1 p24 antigen (absorbance at 450 nm) vs. HIV-1 dilution.
Figure 4:
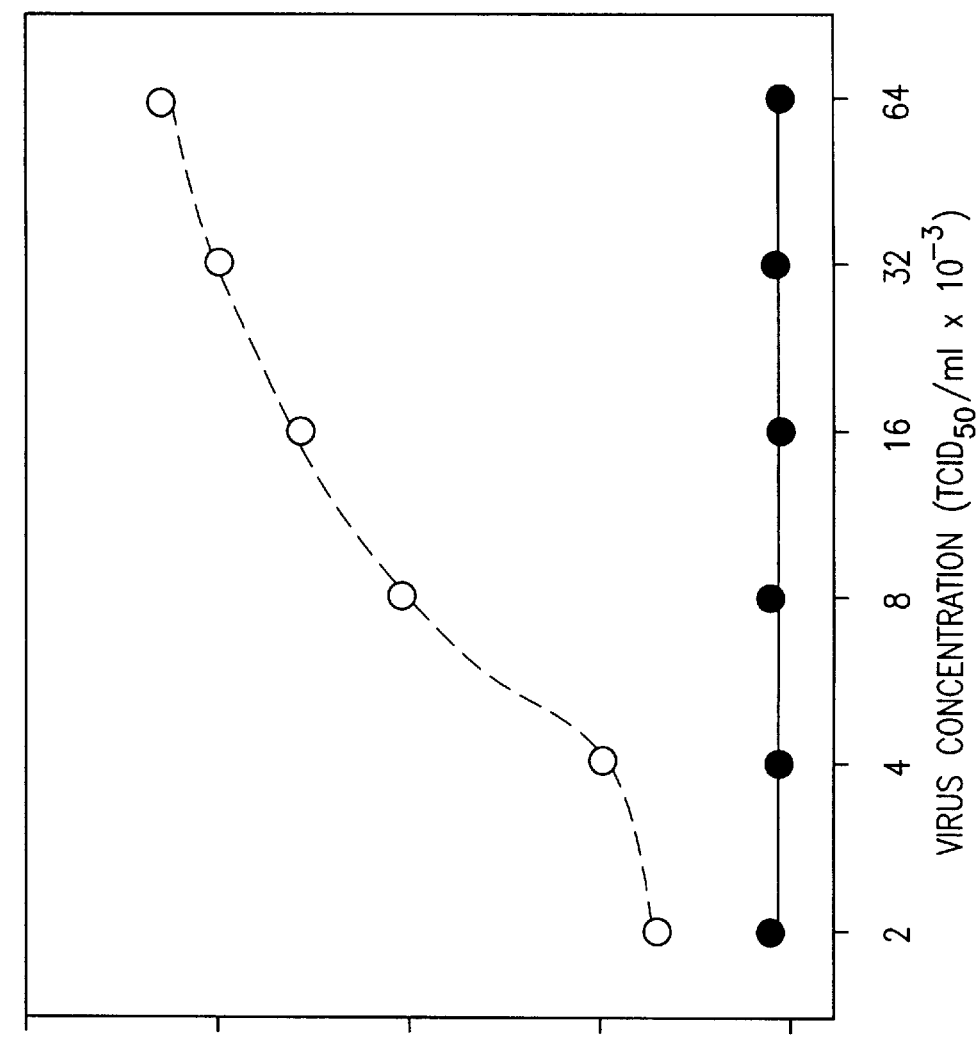
FIG. 4 is a graph of HIV-1 p24 antigen (absorbance at 450 nm) vs. virus concentration.

When a preparation of HIV-1 was mixed 1:1 with either an equal volume of a suspension of "AQUATERIC" in glycerol or with an equal volume of the above-mentioned formulation for 5 minutes at 37° C., a complete loss of HIV-1 infectivity occurred (FIG. 4). The inactivation of HIV-1 infectivity can be ascribed to the complete disruption of HIV-1 virions, as demonstrated by the quantitative release of the internal nucleocapsid antigen p24 (FIG. 3). Similarly, the infectivity of both HSV-1 and HSV-2 was destroyed by suspensions of "AQUATERIC" in glycerol or the "AQUATERIC"-glycerol formulation with PVP and Crospovidone (FIGS. 5 and 6).

With respect of FIG. 3, serial dilutions of untreated and treated HIV-1 were tested for p24 by ELISA. As a positive control, HIV-1 treated with the detergent NP40 was also tested. The results obtained with the "AQUATERIC"-glycerol formulation containing PVP and Crospovidone and N-40 were identical and indicated an 100-fold increase of released p24 antigen, as compared to background levels corresponding to untreated virus. The infectivity of HIV-1 was also eliminated by treatment with the "AQUATERIC"-glycerol formulation containing PVP and Crospovidone.

Figure 5:
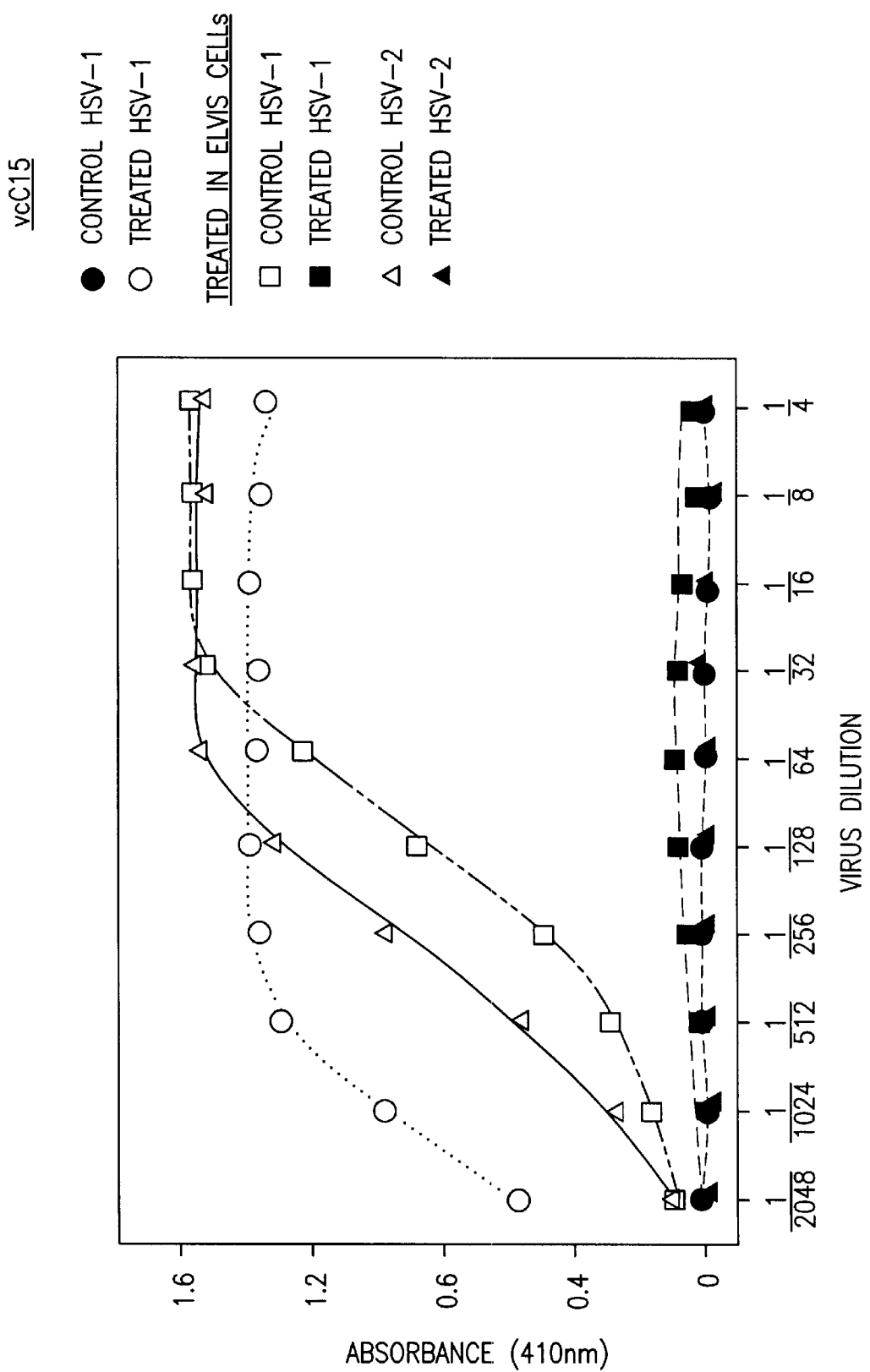
FIG. 5 is a graph of absorbance (410 nm) vs. virus dilution.

Concerning FIG. 5, serial dilutions of the virus preparations before or after treatment with "AQUATERIC" were tested for infectivity using two distinct readout systems based on quantitation of β-galactosidase (absorbance at 410 nm).

Figure 6:
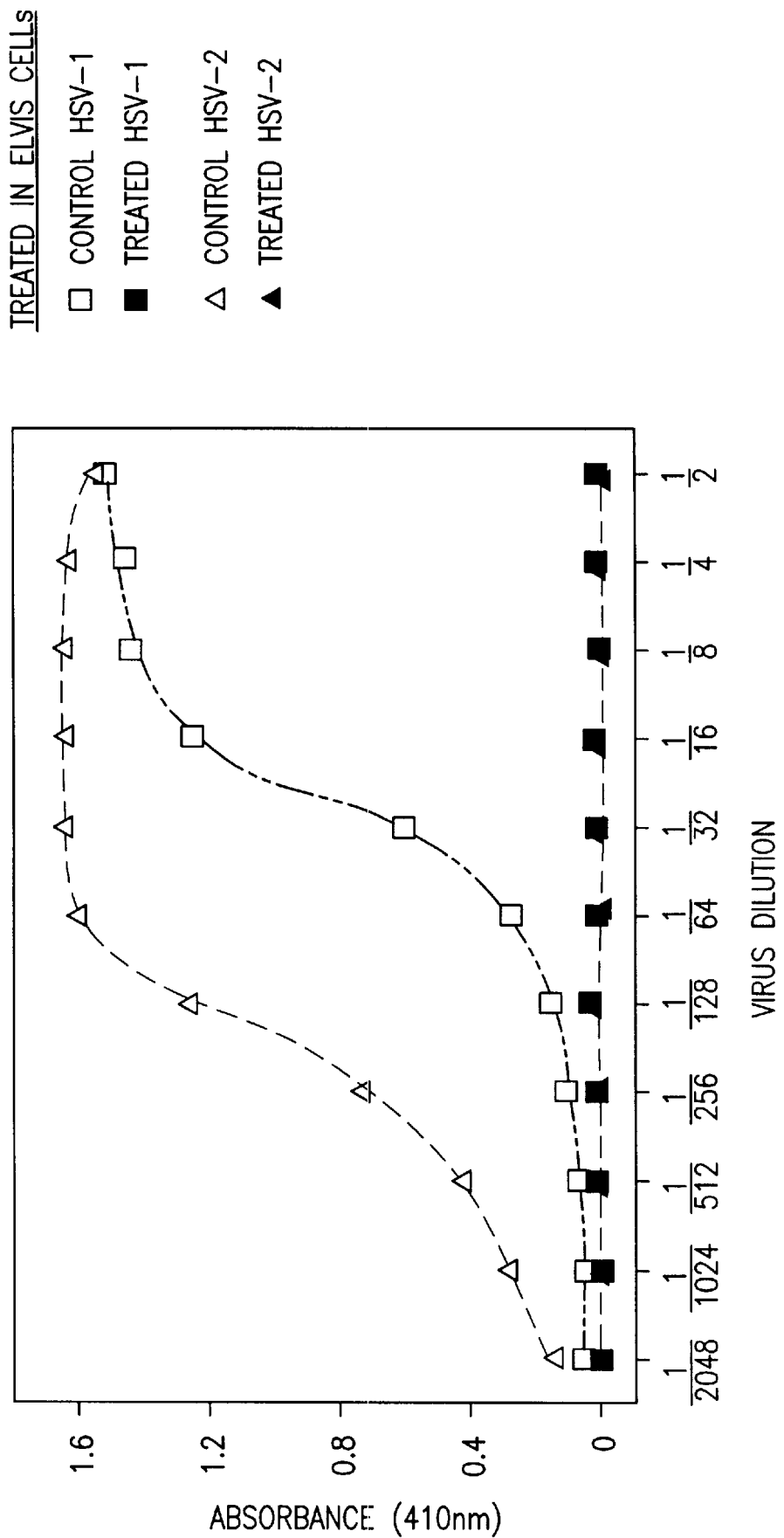
FIG. 6 is a graph of absorbance (410 nm) vs. virus dilution.

Regarding FIG. 6, virus preparations were mixed 1:1 with an "AQUATERIC"-glycerol formulation with PVP and Crospovidone for 5 minutes at 37° C. Serial dilutions of the virus preparations were tested for infectivity using a readout system based on quantitation of β-galactosidase (absorbance at 410 nm).

Figure 7:
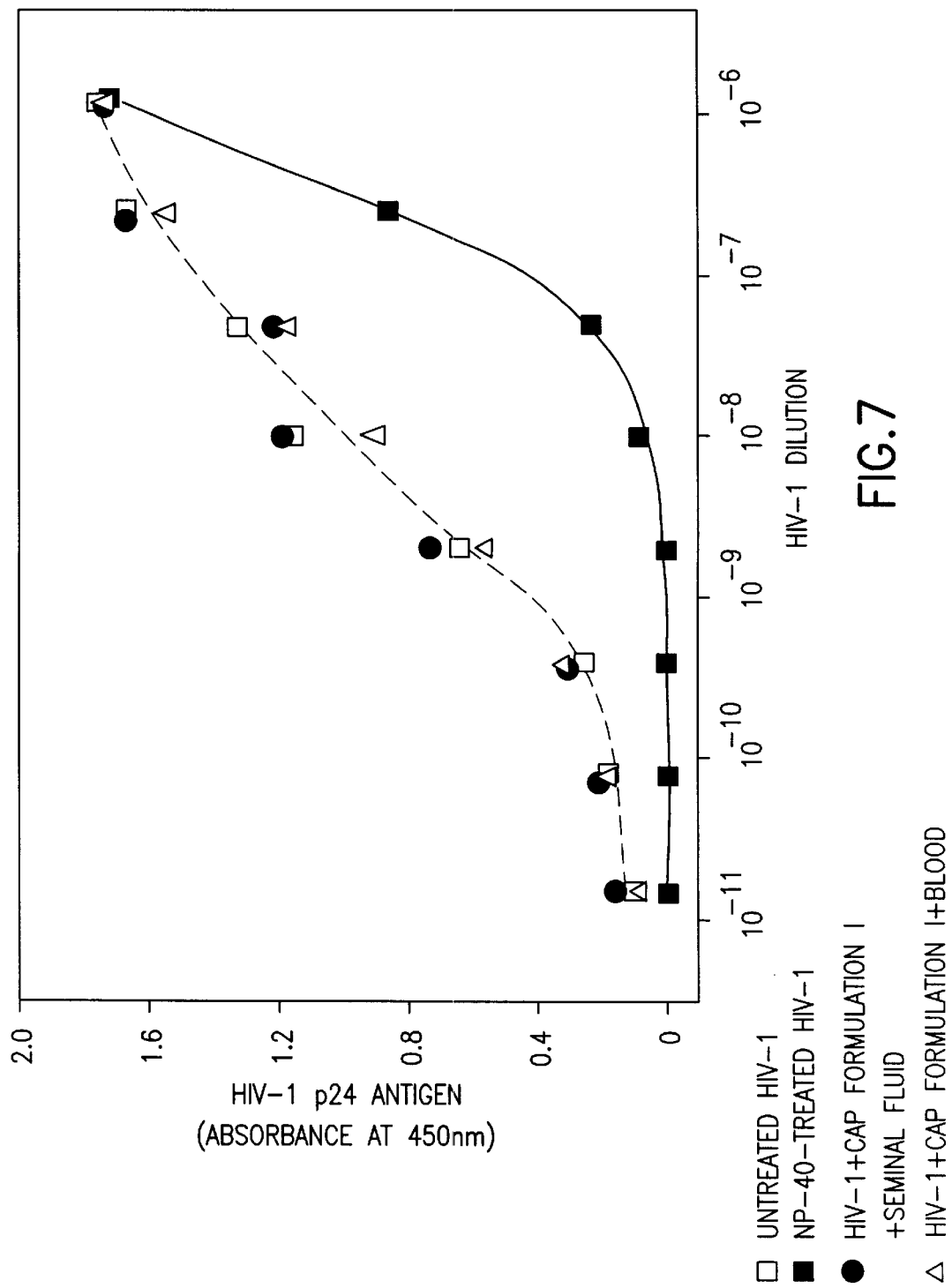
FIG. 7 is a graph which shows the disintegration of purified HIV-1 by treatment with a formulation of micronized CAP in glycerol ("CAP formulation I", which is defined hereinbelow) for 5 minutes at 37° C. in the presence of seminal fluid and whole blood, respectively (for further details see FIG. 3).

CAP as an acetic acid ester of cellulose may undergo hydrolysis in aqueous environments. Therefore, CAP formulations in organic solvents were explored. The best results were obtained by dispersing micronized CAP, containing in addition to CAP a polyoxyethylene-polyoxypropylene block copolymer and distilled acetylated monoglycerides ("AQUATERIC"), in glycerol to which povidone and crospovidone were added to stabilize the suspension (CAP Formulation I). An alternative, CAP Formulation II containing colloidal silicone dioxide, instead of povidone and crospovidone, was also prepared. Mixing of these formulations with an equal volume of a suspension of infectious HIV-1, it was possible to show that this treatment resulted in disintegration of HIV-1 particles measurable by the release of the nucleocapsid antigen p24 (FIG. 3). The CAP Formulation was as effective as the detergent NP40 in releasing the nucleocapsid antigen from virus particles. Similar results were obtained when seminal fluid or whole blood were added to the HIV-CAP formulation mixtures (FIG. 7).

Figure 8:
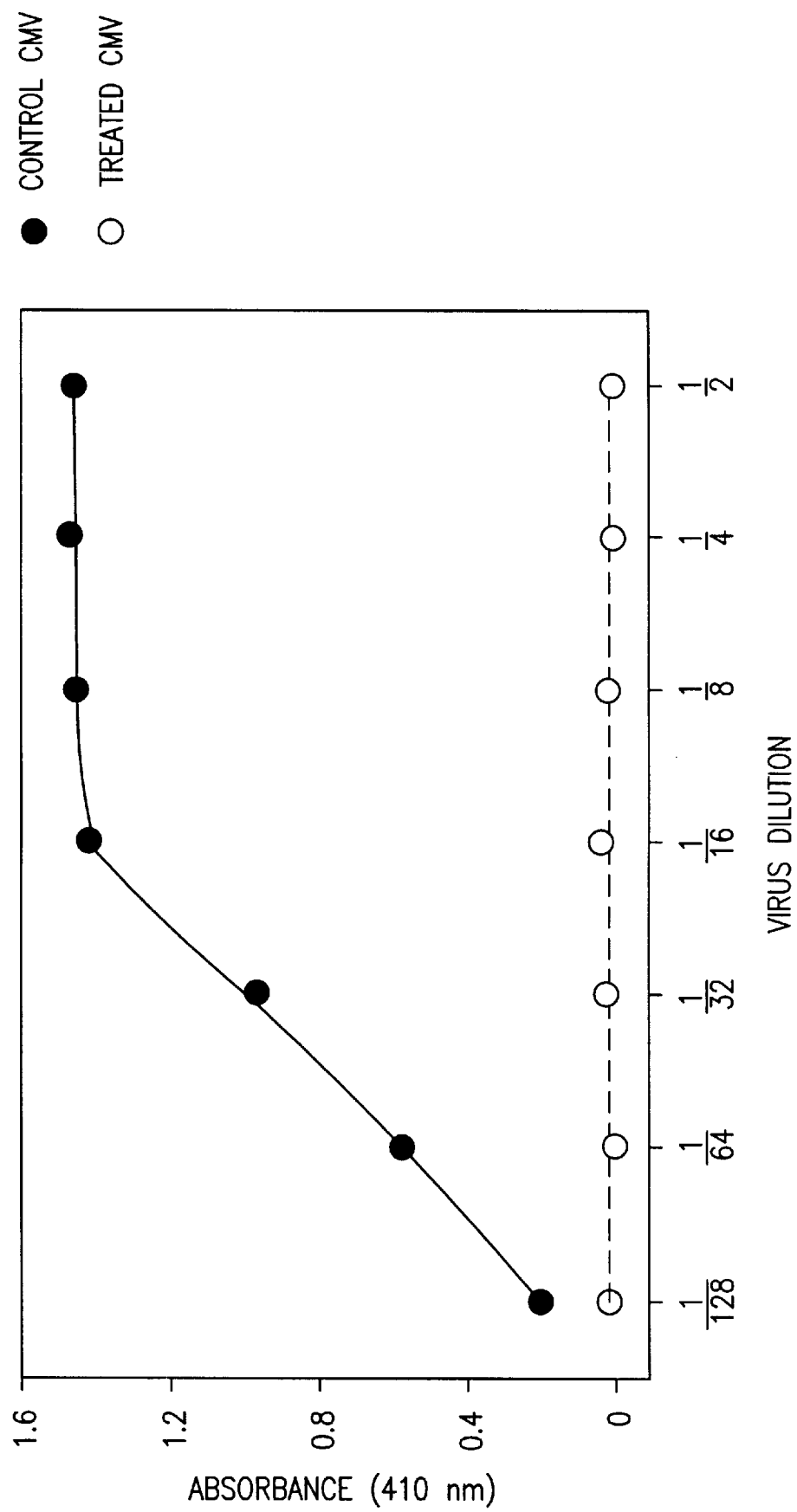
FIG. 8 is a graph which shows the inactivation of CMV by the CAP formulation I. Virus preparations were mixed 1:1 with CAP formulation I for 5 minutes at 37° C. Serial dilutions of the virus preparations were tested for infectivity using a readout system based on the quantitation of β-galactosidase (absorbance at 410 nm).

The CAP Formulations also inactivated the infectivity of HSV-1 and HSV-2 (FIG. 6). Similar results were obtained using HCMV (FIG. 8). Addition of seminal fluid or whole blood to the CAP formulation did not interfere with its virus-inactivating properties under the conditions used, indicating that the microbicidal potential of CAP will be maintained under analogous conditions in vivo.

Example 5
Inactivation of Several Sexually Transmitted Pathogens by CAP Formulations To study the effect of formulated CAD on HIV-1, HSV-1, HSV-2 and HCMV, the respective virus suspensions were mixed with an equal volume of the CAP Formulations I and II (each pre-warmed at 37° C.). After incubation for 5 minutes at 37° C., the suspensions were filtered through a 0.45μ filter and subsequently centrifuged to remove suspended CAP. The supernatant fluids were tested for virus infectivity. This separation could not be accomplished using CAP Formulation II, and the corresponding virus-CAP formulation mixtures were tested directly for virus infectivity. In control experiments, formulations lacking CAP ("AQUATERIC"), mixed with respective virus preparations and PBS (0.14 NaCl, 0.01 M phosphate pH 7.2) mixed with virus were used, respectively. Serial two-fold dilutions of the respective virus preparations were tested for HIV-1 and herpesvirus infectivity using β-galactosidase readout systems for herpesviruses, as described above. In some experiments, seminal fluid (0.6 ml; provided by New England Immunology Associates, Cambridge, Mass.) or whole human heparinized blood (0.11 ml) were added to the CAP Formulations (1 ml), followed by addition of virus (1 ml), in order to evaluate their effect on virus inactivation.

To determine whether or not the CAP Formulations affect the integrity of HIV-1, a preparation of purified virus (strain IIIB; 5 μl; $1.52 \times 10^{10}$ virus particles/ml; Advanced Biotechnologies, Columbia, Md.) was mixed with 45 μl of 0.14 M NaCl and 50 μl of the respective CAP Formulation, each prewarmed to 37° C. After 5 minutes at 37° C., 400 μl of 0.14 M NaCl were added, and the mixture was filtered through a 0.45μ filter prewashed with 0.14 M NaCl, 0.01 M Tris pH 7.2, 0.02 $NaN_3$ (TS). Serial 5-fold dilutions of the filtrate were tested by ELISA for the p24 antigen, as described above. In control experiments, either untreated HIV-1 IIIB or virus treated with the detergent NP40 (final concentration 5 mg/ml; 5 minutes at 37° C.) were equally diluted and tested for the p24 antigen. Similar experiments were done with the CAP Formulations in the presence of seminal fluid or whole human blood (proportions given above). When whole blood was added to the CAP Formulations, the diluted virus preparations were centrifuged at 2000×g for 5 minutes before filtration through 0.45μ filters.

Example 6
Inactivation of Bacterial Pathogens

To test the effect of the CAP Formulation I (a preparation of micronized CAP ("AQUATERIC" containing 66–73% of CAP, a polyoxyethylene-polyoxypropylene block copolymer and distilled acetylated monoglycerides, used in aqueous media as an enteric film-coating liquid (FMC Corporation, Philadelphia, Pa.)), (15.9 g) was mixed with glycerol (70.2 g) and polyvinylpyrrolidone K-30 (Spectrum Quality Products, Inc., New Brunswick, N.J.) (11.1 g) and Crospovidone NF (ISP Technologies, Inc., Wayne, N.J.) (2.8 g) were added in order to maintain the micronized CAP in suspension) on distinct bacterial sexually transmitted disease (STD) pathogens and Lactobacilli, respectively, equal volumes of the CAP Formulation and a suspension of bacteria ($10^8$ to $10^9$ cells/ml in 0.14 M NaCl) were mixed and incubated at 37° C. for either 5 or 15 minutes. Subsequently, 50 μl of 0.43 M $Na_3PO_4.12H_2O$ were added per 1 ml of the suspension. After 5 minutes at room temperature and intermittent mixing, the neutralized suspensions were serially diluted 10-fold in PBS or appropriate broth media. A 20 μl volume of each dilution was inoculated per well of a microtiter plate containing growth media or onto the appropriate agar plate and incubated under appropriate conditions to monitor bacterial growth. Included with each experiment was a positive antibiotic control to demonstrate inhibition of bacterial growth and a control without the formulation or antibiotic to monitor the growth of the bacteria.

The bacterial strains, the corresponding growth media and the control antibiotics used were: *Lactobacillus crispatus*, ATCC 33820 (*lactobacillus* broth; tetracycline 0.5 to 64 μg/ml); *Neisseria gonorroheae*, ATCC 49226 (GC media [Becton Dickinson Microbiology Systems, Sparks, Md.) supplemented with 500 μl of a 2% hemoglobin stock and 10 ml of "ISOVITALEX" (Becton Dickinson Microbiology Systems, Sparks, Md.) per liter of media; Ceftriaxone at 0.005 to 0.128 μg/ml); *Haemophilus ducreyi*, ATCC 33940 (Revised Ducreyi Medium, American Type Culture Collection (ATCC) Culture Medium 1724) supplemented with 10% FBS (Life Technologies, Gaithersburg, Md.) and 1% "ISOVITALEX" (Becton Dickinson Microbiology Systems, Sparks, Md.); Tetracycline 0.125 to 64 μg/ml; *Trichomonas vaginalis*, ATCC 30092 (Modified Fuji media (Ohkawa M., Yamaguchi, K., Tokunaga, S. et al., "The Incidence of Trichomonas Vaginalis in Chromic Prostatis Patients Determined by Culture Using a Newly Modified Liquid Medium", *J. Infect. Dis.*, (1992), 166, 1205–1206); metronidazole 1 to 128 μg/ml).

The guidelines established by the Environmental Protection Agency (Efficacy Data Requirements: Virucides DISITSS-7, Nov. 12, 1981, Modifying AOAC Methods 4.007–4.014, Office of Pesticide Research, Environmental Protection Agency, Washington, D.C.) were followed to study the effect of CAP Formulation I on *Chlamydia trachomatis* (strain LGV type III; ATCC VR-903). After incubation with the formulation and neutralization, the preparation was diluted in DMEM growth media containing 3.6 mM L-glutamine, 45 μg/ml gentamicin and 8.9% FBS, and serial 10-fold dilutions were prepared. The dilutions were added to McCoy cell monolayers (ATCC CRL 1696) and the infection was determined by microscopic observation of cpe, or by staining of inclusion or elementary bodies by iodine staining after 7 days incubation at 37° C. with 55 $CO_2$.

Thus, the above described CAP Formulation I was tested for its inactivating effect on the following sexually transmitted pathogens: *Chlamydia trachomatis, Trichomonas vaginalis, Neisseria gonorrhoeae, Haemophilus ducreyi,* and on *Lactobacillus crispatus*. The results shown in the following Table 7 indicate that all bacteria, except *Lactobacillus crispatus,* lost the capacity to replicate after exposure to the CAP Formulation. The activity of the CAP Formulation against Treponema palladium was not tested because the unavailability of appropriate in vitro assays. Thus, the CAP Formulation was active against four major non-viral STD pathogens, but did not affect Lactobacilli, an essential component of the normal vaginal flora.

TABLE 7

Antibacterial Activity of Formulated CAP

| | Trichomonas vaginalis | | | Neisseris gonorrhoeae | | | Haemophilus ducreyl | | | Lactobacillus crispatus | | | Chiamydis trachomatis | |
|---|---|---|---|---|---|---|---|---|---|---|---|---|---|---|
| Dilution | Growth Control | 5 Min Exposure | 15 Min Exposure | Growth Control | 5 Min Exposure | 15 Min Exposure | Growth Control | 5 Min Exposure | 15 Min Exposure | Growth Control | 5 Min Exposure | 15 Min Exposure | Growth Control | 10 Min Exposure |
| $10^0$ | nd | nd | nd | + | 0 | 0 | + | + | 0 | 5+ | 5+ | 5+ | | |
| $10^{-1}$ | + | 0 | 0 | + | 0 | 0 | + | + | +/− | 5+ | 5+ | 5+ | | |
| $10^{-2}$ | + | 0 | 0 | + | 0 | 0 | + | + | 0 | 5+ | 5+ | 3+ | 4+ | 0 |
| $10^{-3}$ | + | 0 | 0 | + | 0 | 0 | + | + | 0 | 3+ | 4+ | 2+ | 4+ | 0 |
| $10^{-4}$ | + | 0 | 0 | + | 0 | 0 | + | + | 0 | 2+ | 3+ | 2+ | 4+ | 0 |
| $10^{-5}$ | 0 | 0 | 0 | + | 0 | 0 | + | +/− | 0 | 2+ | 2+ | 1+ | 0 | 0 |
| $10^{-6}$ | 0 | 0 | 0 | 0 | 0 | 0 | + | +/− | 0 | 2+ | 1+ | 1+ | 0 | 0 |
| $10^{-7}$ | 0 | 0 | 0 | 0 | 0 | 0 | + | +/− | 0 | 0 | 1+ | 0 | 0 | 0 | nd = not done
"0" = No growth
"+" = Growth
"+/−" = Slight Growth
"1+" = Trace growth
"2+" = Light growth
"3+" = Moderate growth
"4+" = Moderately Dense Growth
"5+" = Dense Growth It will be appreciated that the instant specification is set forth by way of illustration and not limitation, and that various modifications and changes may be made without departure from the spirit and scope of the present invention.

What is claimed is:

1. A method for decreasing the frequency of transmission of human cytomegalovirus, comprising administering to a human an effective anti-cytomegalovirus amount of at least one cellulose phthalate selected from the group consisting of cellulose acetate phthalate and hydroxypropyl methylcellulose phthalate, either alone or in combination with a pharmaceutically acceptable carrier or diluent.

2. A pharmaceutical composition for decreasing the frequency of transmission of a virus selected from the group consisting of human immunodeficiency virus and herpesvirus, or for preventing the transmission of or for treating a sexually transmitted bacterial infection comprising an effective anti-human immunodeficiency virus amount or anti-herpesvirus amount or an effective anti-bacterial amount of a composition comprising (a) 1 to 25 wt. % of a micronized cellulose acetate phthalate, (b) glycerol or squalane, (c) polyvinylpyrrolidone, and (d) cross-linked 1-ethenyl-2-pyrrolidinone homopolymer, wherein the glycerol or squalane, polyvinylpyrrolidone and cross-lined 1-ethenyl-2-pyrrolidinone homopolymer are in amounts such that the composition results in a homogeneous cream.

3. A pharmaceutical composition for decreasing the frequency of transmission of a virus selected from the group consisting of human immunodeficiency virus and herpesvirus, or for preventing the transmission of or for treating a sexually transmitted bacterial infection comprising an effective anti-human immunodeficiency virus amount or anti-herpesvirus amount or anti-bacterial amount of a composition comprising (a) 1 to 25 wt. % of a micronized cellulose acetate phthalate, (b) glycerol or squalane, and (c) colloidal silicon dioxide, wherein the glycerol or squalane and colloidal silicon dioxide are in amounts such that the composition results in a homogeneous cream.

4. A pharmaceutical composition for decreasing the frequency of transmission of a virus selected from the group consisting of human immunodeficiency virus and herpesvirus, or for preventing the transmission of or for treating a sexually transmitted bacterial infection comprising an effective anti-human immunodeficiency virus amount or anti-herpesvirus amount or anti-bacterial amount of a composition comprising (a) micronized cellulose acetate phthalate, (b) glycerol or squalane, and (c) colloidal silicon dioxide and/or polyvinylpyrrolidone and cross-linked 1-ethenyl-2-pyrrolidinone homopolymer, wherein the components (a), (b) and (c) are in amounts such that the composition results in a semi-solid dough or putty.

5. The pharmaceutical composition of claim 3, wherein the micronized cellulose acetate phthalate is prepared by dissolving cellulose acetate phthalate and polyvinylpyrrolidone in dimethyl sulfoxide and then adding water while mixing to form a fine precipitate of cellulose acetate phthalate containing polyvinylpyrrolidone, washing with water and then freeze-drying the resultant powder.

6. The pharmaceutical composition of claim 4, wherein the micronized cellulose acetate phthalate is prepared by dissolving cellulose acetate phthalate and polyvinylpyrrolidone in dimethyl sulfoxide and then adding water while mixing to form a fine precipitate of cellulose acetate phthalate containing polyvinylpyrrolidone, washing with water and then freeze-drying the resultant powder.

7. The pharmaceutical composition of claim 2, wherein (b) is glycerol.

8. The pharmaceutical composition of claim 2, wherein (b) is squalane.

9. The pharmaceutical composition of claim 3, wherein (b) is glycerol.

10. The pharmaceutical composition of claim 3, wherein (b) is squalane.

11. The pharmaceutical composition of claim 4, wherein (b) is glycerol.

12. The pharmaceutical composition of claim 4, wherein (b) is squalane.

13. The pharmaceutical composition of claim 11, wherein (c) is colloidal silicon dioxide.

14. The pharmaceutical composition of claim 12, wherein (c) is colloidal silicon dioxide.

15. The pharmaceutical composition of claim 11, wherein (c) is colloidal silicon dioxide, polyvinylpyrrolidone and cross-linked 1-ethenyl-2-pyrrolidinone.

16. The pharmaceutical composition of claim 12, wherein (c) is colloidal silicon dioxide, polyvinylpyrrolidone and cross-linked 1-ethenyl-2-pyrrolidinone.

17. A method for decreasing the frequency of transmission of a virus selected from the group consisting of human immunodeficiency virus and herpesvirus, or for preventing the transmission of or for treating a sexually transmitted bacterial infection comprising topically administering to a human an effective anti-human immunodeficiency virus amount or anti-herpesvirus amount or an effective anti-bacterial amount of the pharmaceutical composition of claim 2.

18. A method for decreasing the frequency of transmission of a virus selected from the group consisting of human immunodeficiency virus and herpesvirus, or for preventing the transmission of or for treating a sexually transmitted bacterial infection comprising topically administering to a human an effective anti-human immunodeficiency virus amount or anti-herpesvirus amount or an effective anti-bacterial amount of the pharmaceutical composition of claim 3.

19. A method for decreasing the frequency of transmission of a virus selected from the group consisting of human immunodeficiency virus and herpesvirus, or for preventing the transmission of or for treating a sexually transmitted bacterial infection comprising topically administering to a human an effective anti-human immunodeficiency virus amount or anti-herpesvirus amount or an effective anti-bacterial amount of the pharmaceutical composition of claim 4.

20. The method of claim 1, wherein the at least one cellulose phthalate is cellulose acetate phthalate.

21. The method of claim 1, wherein the at least one cellulose phthalate is hydroxypropyl methylcellulose phthalate.

22. The method of claim 1, wherein said cellulose phthalate is a combination of cellulose acetate phthalate and hydroxypropyl methylcellulose phthalate.

23. The method of claim 17, wherein the virus is HIV-1.

24. The method of claim 18, wherein the virus is HIV-1.

25. The method of claim 19, wherein the virus is HIV-1.

26. The method of claim 17, wherein the virus is a herpesvirus.

27. The method of claim 26, wherein the herpesvirus is HSV-1.

28. The method of claim 26, wherein the herpesvirus is HSV-2.

29. The method of claim 18, wherein the virus is a herpesvirus.

30. The method of claim 29, wherein the herpesvirus is HSV-1.

31. The method of claim 29, wherein the herpesvirus is HSV-2.

32. The method of claim 19, wherein the virus is a herpesvirus.

33. The method of claim 32, wherein the herpesvirus is HSV-1.

34. The method of claim 32, wherein the herpesvirus is HSV-2.

35. The method of claim 1, wherein the administering is by topical administration.

36. The pharmaceutical composition of claim 2, wherein the micronized cellulose acetate phthalate is in an amount of 5 to 20 wt. %.

37. The pharmaceutical composition of claim 2, wherein the micronized cellulose acetate phthalate is in an amount of 12 to 18 wt. %.

38. The pharmaceutical composition of claim 3, wherein the micronized cellulose acetate phthalate is in an amount of 5 to 20 wt. %.

39. The pharmaceutical composition of claim 3, wherein the micronized cellulose acetate phthalate is in an amount of 12 to 18 wt. %.

40. The pharmaceutical composition of claim 2, wherein the micronized cellulose acetate phthalate is prepared by dissolving cellulose acetate phthalate and polyvinylpyrrolidone in dimethyl sulfoxide and then adding water while mixing to form a fine precipitate of cellulose acetate phthalate containing polyvinylpyrrolidone, washing with water and then freeze-drying the resultant powder.

41. The pharmaceutical composition of claim 3, wherein the micronized cellulose acetate phthalate is in an amount of 5 to 20 wt. %.

42. The pharmaceutical composition of claim 3, wherein the micronized cellulose acetate phthalate is in an amount of 12 to 18 wt. %.

43. The pharmaceutical composition of claim 4, wherein the micronized cellulose acetate phthalate is in an amount of 5 to 20 wt. %.

44. The pharmaceutical composition of claim 4, wherein the micronized cellulose acetate phthalate is in an amount of 12 to 18 wt. %.

45. The pharmaceutical composition of claim 3, wherein the micronized cellulose acetate phthalate is prepared by dissolving cellulose acetate phthalate and polyvinylpyrrolidone in dimethyl sulfoxide and then adding water while mixing to form a fine precipitate of cellulose acetate phthalate containing polyvinylpyrrolidone, washing with water and then freeze-drying the resultant powder.

* * * * *

UNITED STATES PATENT AND TRADEMARK OFFICE
CERTIFICATE OF CORRECTION

| | |
|---|---|
| PATENT NO. | : 6,165,493 |
| APPLICATION NO. | : 09/175909 |
| DATED | : December 26, 2000 |
| INVENTOR(S) | : Alexander Robert Neurath et al. |

It is certified that error appears in the above-identified patent and that said Letters Patent is hereby corrected as shown below:

Claim 5, column 35, line 52, repalce "3" with --2--.

Signed and Sealed this

Twenty-second Day of August, 2006

JON W. DUDAS
*Director of the United States Patent and Trademark Office*

UNITED STATES PATENT AND TRADEMARK OFFICE
CERTIFICATE OF CORRECTION

PATENT NO. : 6,165,493 Page 1 of 1
APPLICATION NO. : 09/175909
DATED : December 16, 2000
INVENTOR(S) : Alexander Robert Neurath et al.

It is certified that error appears in the above-identified patent and that said Letters Patent is hereby corrected as shown below:

Claims 40 to 44, column 38, lines 5 to 15, delete in their entirety and replace with the following claims:

40. A method for preventing the transmission of or treating a sexually transmitted bacterial infection comprising administering to a human an effective anti-bacterial amount of at least one cellulose phthalate selected from the group consisting of cellulose acetate phthalate and hydroxypropyl methylcellulose phthalate, either alone or in combination with a pharmaceutically acceptable carrier or diluent.

41. The method of claim 40, wherein the at least one cellulose phthalate is cellulose acetate phthalate.

42. The method of claim 40, wherein the at least one cellulose phthalate is hydroxypropyl methylcellulose phthalate.

43. The method of claim 40, wherein said cellulose phthalate is a combination of cellulose acetate phthalate and hydroxypropyl methylcellulose phthalate.

44. The method of claim 40, wherein the bacterial infection is selected from the group consisting of *Trichomonas vaginalis*, *Neisseria gonorrhoeae*, *Haemophilus ducreyi*, *Lactobacillus crispatus* and *Chlamydia trachomatis*.

Signed and Sealed this

Seventh Day of August, 2007

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,165,493 | Page 1 of 1 |
| APPLICATION NO. | : 09/175909 | |
| DATED | : December 26, 2000 | |
| INVENTOR(S) | : Alexander Robert Neurath et al. | |

It is certified that error appears in the above-identified patent and that said Letters Patent is hereby corrected as shown below:

Claims 40 to 44, column 38, lines 5 to 15, delete in their entirety and replace with the following claims:

40. A method for preventing the transmission of or treating a sexually transmitted bacterial infection comprising administering to a human an effective anti-bacterial amount of at least one cellulose phthalate selected from the group consisting of cellulose acetate phthalate and hydroxypropyl methylcellulose phthalate, either alone or in combination with a pharmaceutically acceptable carrier or diluent.

41. The method of claim 40, wherein the at least one cellulose phthalate is cellulose acetate phthalate.

42. The method of claim 40, wherein the at least one cellulose phthalate is hydroxypropyl methylcellulose phthalate.

43. The method of claim 40, wherein said cellulose phthalate is a combination of cellulose acetate phthalate and hydroxypropyl methylcellulose phthalate.

44. The method of claim 40, wherein the bacterial infection is selected from the group consisting of *Trichomonas vaginalis*, *Neisseria gonorrhoeae*, *Haemophilus ducreyi*, *Lactobacillus crispatus* and *Chlamydia trachomatis*.

This certificate supersedes Certificate of Correction issued August 7, 2007.

Signed and Sealed this

Fourth Day of September, 2007

JON W. DUDAS
*Director of the United States Patent and Trademark Office*